US008541246B2

(12) United States Patent
Bunce et al.

(10) Patent No.: US 8,541,246 B2
(45) Date of Patent: Sep. 24, 2013

(54) SAMPLE PLATE SYSTEMS AND METHODS

(75) Inventors: Adrian Bunce, Worthing (GB); Andrew Fusellier, Torteva (GB)

(73) Assignee: Dynex Technologies, Inc., Chantilly, VA (US)

(*) Notice: Subject to any disclaimer, the term of this patent is extended or adjusted under 35 U.S.C. 154(b) by 329 days.

(21) Appl. No.: 12/846,580

(22) Filed: Jul. 29, 2010

(65) Prior Publication Data

US 2011/0027914 A1 Feb. 3, 2011

(30) Foreign Application Priority Data

Jul. 29, 2009 (GB) .................................. 0913258.0
Oct. 7, 2009 (GB) .................................. 0917555.5
Apr. 13, 2010 (GB) .................................. 1006087.9

(51) Int. Cl.
*G01N 33/543* (2006.01)
(52) U.S. Cl.
USPC ....................................................... 436/518
(58) Field of Classification Search
None
See application file for complete search history.

(56) References Cited

U.S. PATENT DOCUMENTS

| | | | |
|---|---|---|---|
| 4,415,098 A | 11/1983 | Haas | |
| 4,681,742 A | 7/1987 | Johnson et al. | |
| 5,620,853 A | 4/1997 | Smethers et al. | |
| 6,429,027 B1 | 8/2002 | Chee et al. | |
| 6,602,702 B1 * | 8/2003 | Anslyn et al. | 435/288.7 |
| 6,649,403 B1 | 11/2003 | McDevitt et al. | |
| 6,770,441 B2 | 8/2004 | Dickinson et al. | |
| 6,858,394 B1 | 2/2005 | Chee et al. | |
| 6,859,570 B2 | 2/2005 | Walt et al. | |
| 6,998,274 B2 | 2/2006 | Chee et al. | |
| 2003/0091475 A1 | 5/2003 | Yu et al. | |
| 2003/0186228 A1 | 10/2003 | McDevitt et al. | |
| 2004/0185482 A1 | 9/2004 | Stuelpnagel et al. | |
| 2004/0241776 A1 | 12/2004 | Geister et al. | |
| 2005/0079621 A1 | 4/2005 | Elmes et al. | |
| 2005/0130318 A1 | 6/2005 | Vann et al. | |
| 2006/0012130 A1 | 1/2006 | Vann et al. | |
| 2006/0272738 A1 | 12/2006 | Lim et al. | |
| 2006/0275178 A1 | 12/2006 | Chang et al. | |
| 2007/0059218 A1 * | 3/2007 | Kane | 422/101 |
| 2007/0231824 A1 | 10/2007 | Chee et al. | |
| 2008/0039343 A1 | 2/2008 | Guire et al. | |
| 2008/0182248 A1 | 7/2008 | Fan et al. | |
| 2008/0220982 A1 | 9/2008 | Vu | |
| 2009/0069200 A1 | 3/2009 | Yu | |
| 2009/0123336 A1 | 5/2009 | Yang et al. | |
| 2009/0163378 A1 | 6/2009 | Mehrpouyan et al. | |
| 2009/0298716 A1 | 12/2009 | Stuelpnagel et al. | |
| 2010/0075865 A1 | 3/2010 | Trau et al. | |
| 2011/0263463 A1 * | 10/2011 | Rothberg et al. | 506/39 |
| 2013/0071915 A1 * | 3/2013 | Bustillo et al. | 435/287.2 |

FOREIGN PATENT DOCUMENTS

| | | |
|---|---|---|
| AU | 775056 B2 | 7/2004 |
| CA | 2170249 A1 | 3/1995 |
| EP | 0087899 B1 | 12/1986 |
| EP | 0715719 B1 | 4/2000 |
| EP | 1171230 B1 | 11/2002 |
| EP | 1141712 B1 | 7/2005 |
| EP | 1153303 B1 | 9/2006 |
| EP | 1434055 B1 | 9/2006 |
| EP | 1722236 A1 | 11/2006 |
| EP | 2045601 A1 | 4/2009 |
| EP | 1593967 B1 | 7/2009 |
| JP | 10332593 | 12/1998 |
| JP | 2000-346842 A | 12/2000 |
| JP | 2007-285828 A | 11/2007 |
| JP | 2009-195160 A | 9/2009 |
| RU | 2262939 C2 | 10/2005 |
| RU | 2284035 C2 | 9/2006 |
| SU | 1530242 A1 | 12/1989 |
| WO | WO 92/01513 A1 | 2/1992 |
| WO | WO 01/58482 A1 | 8/2001 |
| WO | WO 02/30561 A2 | 4/2002 |
| WO | WO 02/30561 A3 | 5/2003 |
| WO | WO 03/036263 A2 | 5/2003 |
| WO | WO 03/036263 A3 | 10/2003 |
| WO | WO 2004/111260 A2 | 12/2004 |
| WO | WO 2004/111260 A3 | 11/2005 |
| WO | WO 2006/102321 A2 | 9/2006 |
| WO | WO 2007/067680 A2 | 6/2007 |
| WO | WO 2007/067680 A3 | 8/2007 |
| WO | WO 2006/102321 A3 | 9/2007 |
| WO | WO 2009/029561 A2 | 3/2009 |
| WO | WO 2009/029561 A3 | 5/2009 |
| WO | WO 2010/008519 A2 | 1/2010 |
| WO | WO 2010/008519 A3 | 5/2010 |

OTHER PUBLICATIONS

U.S. Appl. No. 13/463,507, filed May 3, 2012, Bunce et al.
U.S. Appl. No. 13/187,791, filed Jul. 21, 2011, Bunce et al.
Dunbar et al. Customized Probe and Primer Design for SNP Detection: Development of FlexMAPTM Microsphere-Based Assays on the Luminex® Platform Using DNASIS® MAX Software. Technical Bulletin presented at PharmaDiscovery, May 10-12, Washington, DC, 2005.
European search report dated Nov. 10, 2011 for Application No. 10275038.7.
International search report dated Jan. 4, 2011 for PCT/US2010/001443.
Miller et al. Basic concepts of microarrays and potential applications in clinical microbiology. Clin Microbiol Rev 2294:611-633, 2009.
Notice of invitation to pay additional fees dated Nov. 5, 2011 for PCT application No. GB2010/001443.
Office action and search report dated Nov. 24, 2009 for Application No. GB 0913258.0.
Office action dated Jul. 28, 2011 for Application No. GB 1006087.9.
European office action dated Sep. 15, 2011 for Application No. 10275038.7.
International search report and written opinion dated Sep. 16, 2011 for PCT/GB2011/051383.

* cited by examiner

*Primary Examiner* — Ann Lam
(74) *Attorney, Agent, or Firm* — Diederiks & Whitelaw PLC

(57) ABSTRACT

A sample plate comprising a sample well is disclosed. The sample well can comprise one or more bead retaining chambers. Also provided herein is a method of using the sample plate and kits comprising the sample plate.

34 Claims, 19 Drawing Sheets

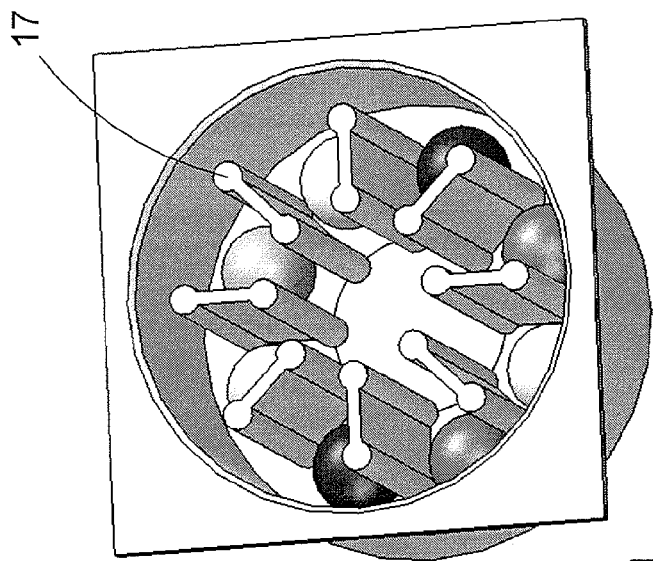
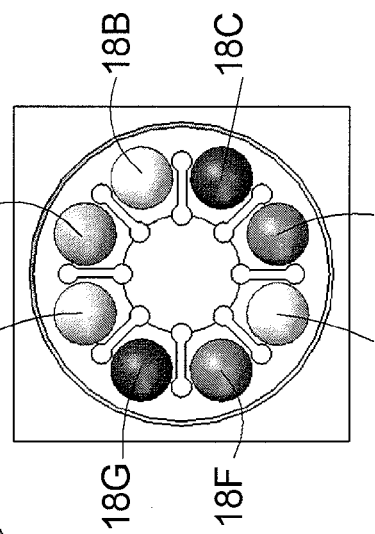
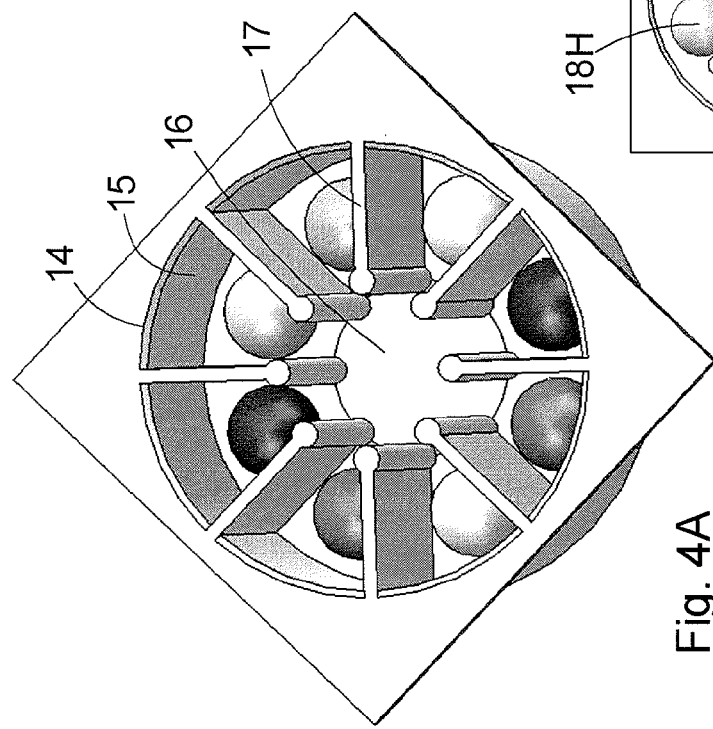
Fig. 4B
Fig. 4C
Fig. 4A

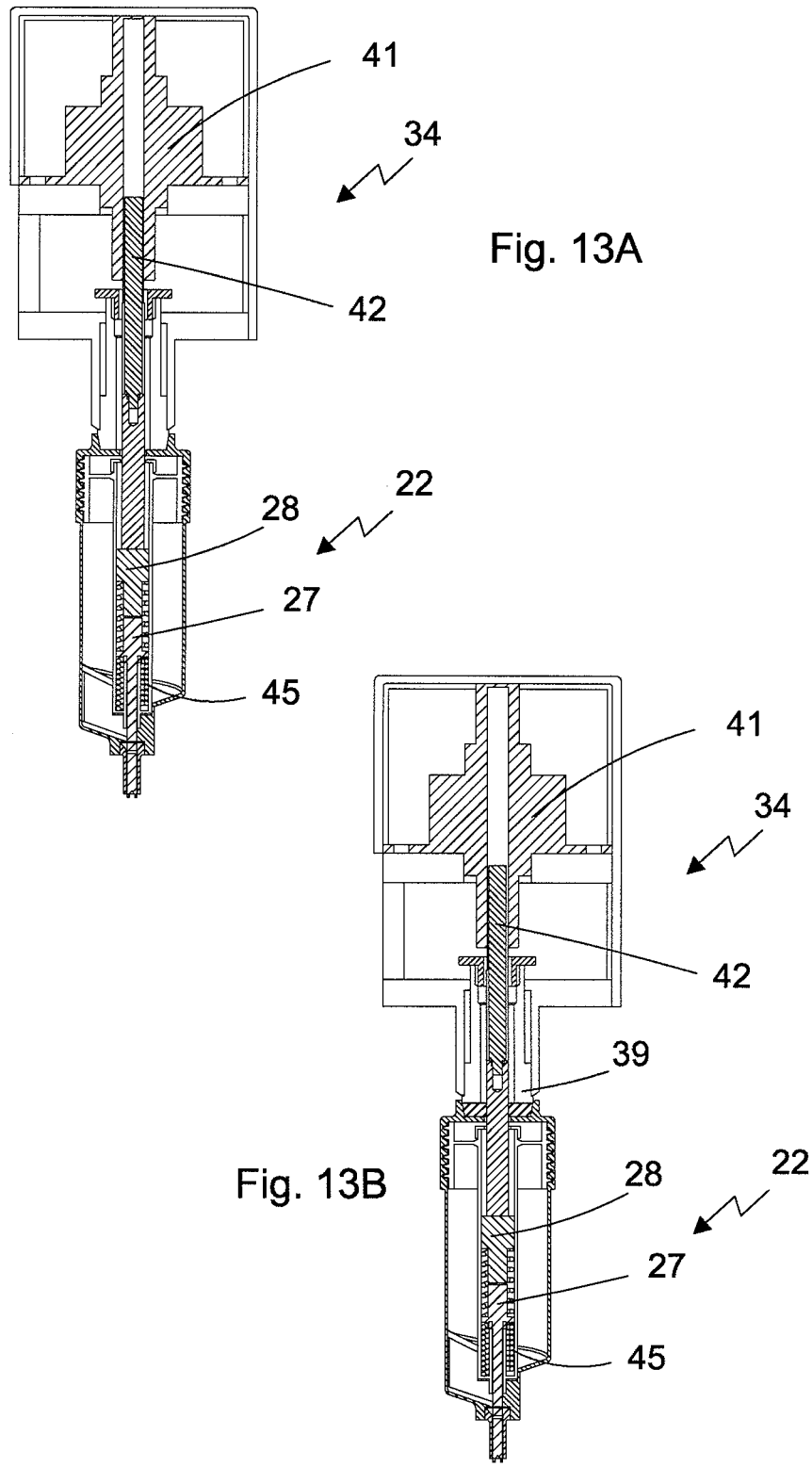

SAMPLE PLATE SYSTEMS AND METHODS

CROSS-REFERENCE

This application claims the benefit of U.K. application numbers GB 0913258.0, filed Jul. 29, 2009, GB 0917555.5, filed Oct. 7, 2009, and GB 1006087.9, filed Apr. 13, 2010, which are incorporated herein by reference in their entirety.

BACKGROUND

An assay device is important in many biological assays, such as for detecting an analyte in a liquid sample. A desirable feature of an assay device is the durability of the plate and maintenance of the reagent in the plate for accurate assay results. For example, a design for an assay device is a sample plate comprising molded wells with fingers that protrude up from the bottom of the well and into which a reagent bead is dispensed, and the reagent bead can be captured in the fingers. However, as reagent beads are free to move up and down within the finger height, a reagent bead may become stuck at an undesired height during a processing or reading step, which can lead to an inaccurate assay result. Furthermore, any movement of, or damage to, the fingers could result in a reagent bead becoming stuck at an undesired height. The fingers also protrude from the base which makes them susceptible to damage particularly during pipetting and washing stages.

Another desirable feature of an assay device is the ability to perform multiple assays at once, or the ability to multiplex. For example, an assay device with a high density of wells for a sample plate allows an increased number of assays to be performed on a single plate. Another desirable characteristic of an assay device is the ability to use a minimal amount of reagents and sample, as well as the prevention of crosstalk between different samples during multiplexing.

Another desirable aspect of an assay device is the ease in manufacturing. For example, a sample well with molded fingers is relatively complex to manufacture and can suffer from unreliability issues during manufacture. The long thin fingers are difficult to form by molding and would be prone to damage during manufacture or during use. The fingers also have a feature at the top which in a mould tool would be an undercut. When the part is ejected off the tool the fingers must bend for the feature to get past the tool material. Such a manufacturing process is generally undesirable due to unreliability issues. Furthermore, any change in the process parameters is likely to affect the ability to release the part from the tool and leave the part intact to the correct mechanical tolerances. The position of the fingers relative to each other would be critical to allow the reagent bead to move up and down correctly and also to ensure that the reagent bead does not come out of the top of the fingers. This would be very difficult, in practice, to control in a mass production environment. The design of the single bead arrangement is also completely different to the design of the multi-well arrangement. As a result, completely different tool designs would be required which again would greatly increase the complexity of manufacture. In a high volume manufacturing environment the combination of the design features and quality assurance concerns would make the sample plates excessively expensive to produce.

Thus, there is a need for an assay device with one or more of these desirable features. Provided herein is a sample plate system, and methods of using the system, that meets these needs and provides related advantages as well.

SUMMARY

The present disclosure provides an assay device system and methods of using the system. In one aspect, a sample plate system and methods of using the system is provided herein. In one embodiment, the sample plate comprises one or more sample wells, such as a plurality of sample wells. The one or more sample wells can comprise a base portion; wherein the base portion comprises one or more recesses, such as a plurality of recesses. In another embodiment, the sample well comprises one or more beads. In one embodiment, the one or more recesses comprise a tapered section. The tapered section can have a taper of at least about 1°, such as between 1° and 15°. In one embodiment, the tapered section has a taper of 2-4°; 4-6°; 6-8°; or 8-10°. In another embodiment, the one or more recesses comprise a diameter less than a diameter of a bead, such as a bead present in the well or to be dispensed or deposited into the sample well. For example, the diameter of one or more recesses can be at least about 5% smaller than the diameter of the bead. In one embodiment, the bead present in a well does not touch or contact the bottom surface or base portion of the well or recess.

In another embodiment, the one or more recesses comprise a countersunk portion. The one or more sample wells can comprise at least 2 recesses, such as between 2 and 20 recesses. In one embodiment, the one or more sample wells comprise at least 10 recesses. The one or more recesses can be arranged circumferentially around a central portion of said sample well. In one embodiment, the central portion comprises a central recess. In another embodiment, the central portion does not comprise a recess.

The one or more recesses can also be arranged in a substantially symmetrical or regular manner, in a substantially asymmetrical or irregular manner, in a substantially linear manner, or in a substantially curved manner.

In one embodiment, the sample wells of the sample plate are arranged in an A×B format, wherein A and B are perpendicular axes. The number of wells along the A axis can be greater than, less than, or equal to the number of wells along the B axis. The number of wells along the A axis or B axis can be at least 2. In one embodiment, the number of wells along the A axis or B axis is between 2 and 15.

The sample plate can comprise a sample well that is connected to another sample well by a frangible region. The sample plate can also comprise a base comprising a docking portion for securing the sample plate to a corresponding docking portion of a plate frame holder.

The sample plate disclosed herein can also comprise a probe. The probe can be attached to a bead. The probe can be a nucleic acid, antibody, antibody fragment, protein, peptide, aptamer, or chemical compound. In one embodiment, the probe comprises an oligonucleotide. In one embodiment, the sample plate comprises a plurality of probes, wherein a subset of the plurality differs from another subset of said plurality. In yet another embodiment, the plurality of probes comprises at least 3 different probes.

Also provided herein is a bead dispensing system comprising: a sample plate as disclosed herein; a bead dispenser; and a control system configured to control dispensing of a plurality of reagent beads from said reagent bead dispenser into one or more sample wells of said sample plate. The bead dispenser can comprise one or more bead. In one embodiment, the bead dispenser comprises: a syringe body comprising an annular chamber surrounding a longitudinal bore, wherein the annular chamber is configured to channel a reagent bead within the annular chamber towards a chamber provided in the bore; a plunger provided within the longitudinal bore; and a barrel or nozzle, wherein the plunger is configured to dispense a bead from the chamber into the barrel or nozzle. In one embodiment, the bead dispensing system is configured to dispense a bead automatically.

In yet another aspect of the present disclosure, a method of dispensing beads comprising: providing a bead dispenser comprising one or more beads; providing a sample plate comprising one or more sample wells, wherein one or more of the sample wells comprise a base portion; wherein said base portion comprises one or more recesses with a tapered section or a diameter less than the diameter of a bead being dispensed into the sample well or present in the sample well; and controlling the dispensing of one or more beads from the bead dispenser into one or more of the sample wells, is also provided. In one embodiment, the dispensing is performed automatically A kit for detecting an analyte comprising one or more sample plates as disclosed herein and a plurality of beads is also provided herein. In one embodiment, the plurality of beads comprises one or more probes. The probe can be a nucleic acid, antibody, antibody fragment, protein, peptide, aptamer, or chemical compound. In one embodiment, the probe is an oligonucleotide.

Also provided herein is a method of detecting an analyte comprising: adding a sample to a sample plate disclosed herein and detecting binding of an analyte in the sample with the probe. In one embodiment, the method comprises a sample plate comprising a plurality of probes and a plurality of analytes is detected. In yet another embodiment, a plurality of samples is added to the sample plate.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the invention are utilized, and the accompanying drawings of which:

FIG. 4 shows configurations of a sample well of a sample plate with radial wall members. A) shows a first configuration of a sample well of a sample plate with radial wall members depending from the other or inner wall, B) shows a configuration of a sample well of a sample plate where radial wall members to not depend from the wall of the sample well; C) illustrates how different species or types of reagent beads or microspheres may be dispensed into different reagent bead or microsphere receiving chambers or sections of a sample well of a sample plate.

FIG. 13 shows a reagent bead or microsphere syringe A) in the process of being ejected from the reagent bead or microsphere syringe pick-up device and B) having been ejected from the reagent bead or microsphere pick-up device.

DETAILED DESCRIPTION

Figure 1:
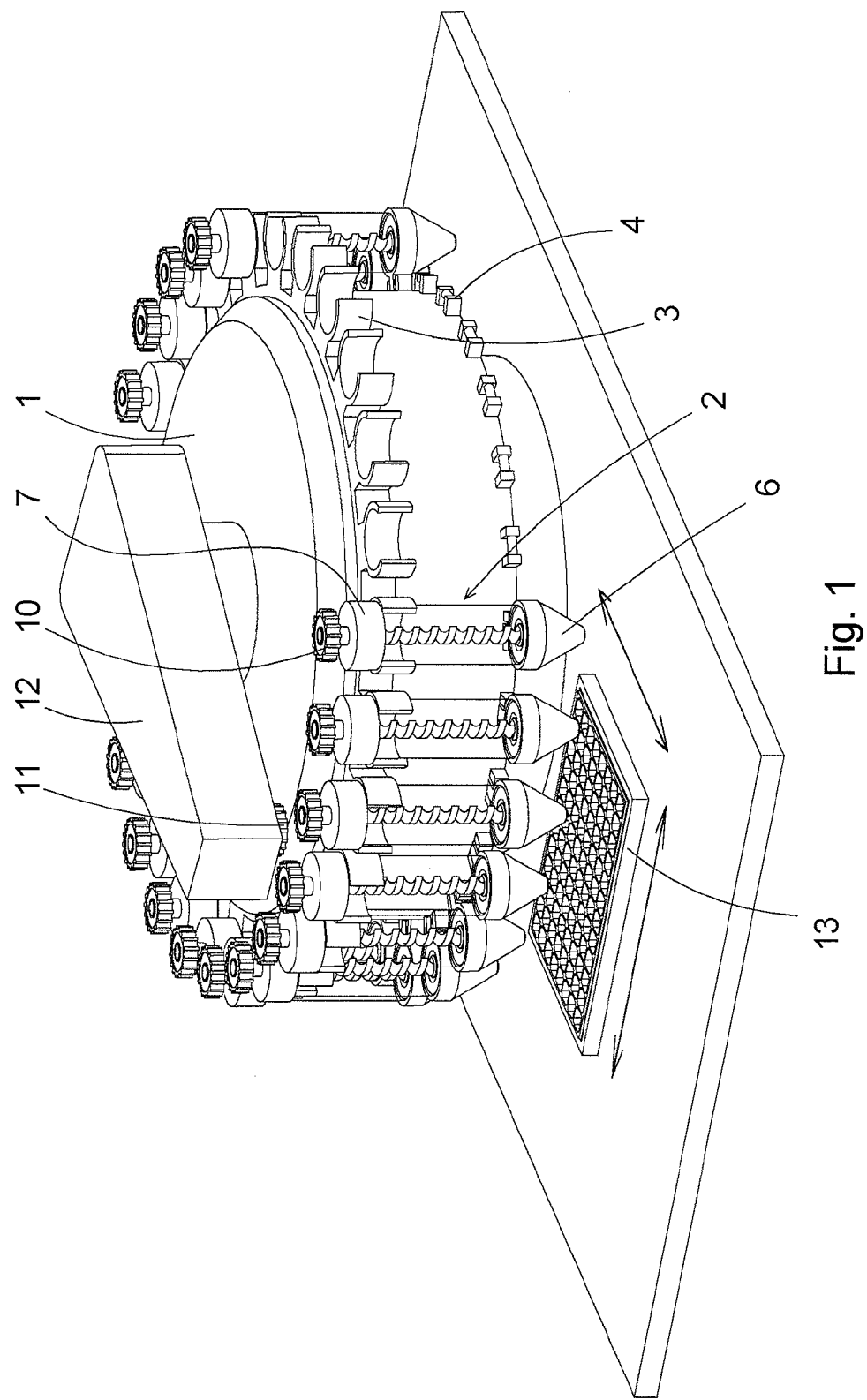
FIG. 1 shows a first main embodiment of the present invention wherein a plurality of reagent bead or microsphere dispensers are attached to a rotatable carousel and a sample plate is mounted on a translation stage below an arm which extends from the rotatable carousel and which is engaged with a reagent bead or microsphere dispenser.

The present disclosure provides an assay device and methods of using the device. The assay device comprises one or beads, which can be dispensed by a bead dispenser as disclosed herein. Furthermore the assay device can comprise one or more probes, such as a probe attached to a bead, which can be used to detect an analyte. The assay device can be a sample plate, which comprises one or more wells. Each well can comprise one or more probes, which can be used to detect one or more analytes of a sample. The one or more probes can be attached to a bead. Furthermore the sample plate can be used to assay a plurality of samples.

The sample plate can be used with known automated microplate processing systems. In one embodiment, with some hardware modification. Yet in another embodiment, the sample plate can be used with known automated microplate processing systems without requiring any hardware modifications. For example, the sample well can be a cylinder having proportions which are similar to that of a well of a conventional microplate so the fluid and other handling characteristics of the sample well are well known. Processing steps according such as pipetting, mixing, washing and incubation can thus follow the same type of fluid characteristics that conventional microplates go through, but with the use of the sample plate disclosed herein.

The sample plate can also be relatively simple and easy to manufacture as compared with other known arrangements. The sample plate can be manufactured by moulding using an open and shut tool so that the manufacturability is high and reliable. The injection mould tool design used to form the sample plates can be simple. For example, it may not require the use of undercuts or thin features to mould. As a result, the production of sample plates having different formats can be readily achieved. A tool that produces a sample well with 6 pockets or bores can be readily adapted to produce a sample well having a different number (e.g. 21) of pockets.

The sample plate can also be easily validated with different well designs and formats as the test protocols can remain essentially the same. In one embodiment, pipetting and incubation is not changed and the washing procedure may require a minor alteration to the aspirate routine.

Sample Plate

In one embodiment, the sample plate comprises one or more sample wells. The sample plate can comprise one sample well or a plurality of sample wells. For example, a sample plate can comprise at least 1, 2, 3, 4, 5, 6, 7, 8, 9, 10, 20, 30, 40, 50, 60, 70, 80, 90, 100, 200, 300, 400, 500, 600, 700, 800, 900, or 1000 wells. In one embodiment, a sample plate can comprise wells in multiples of 2s, 3s, 4s, such as a sample plate comprising 2, 3, 4, 6, 8, 12, 16, 24, 32, 36, 96, 384, or 1536 wells.

The sample plate can be fabricated from a polymer such as polystyrene, PVC, Perspex or Lucite. In one embodiment, the sample plate is a microplate, measuring approximately 5 inches (12.7 cm) in length, 3.3 inches (8.5 cm) in width, and 0.55 inches (1.4 cm) in depth. In one embodiment the sample plate is transparent, such as made from polystyrene. In yet another embodiment, the sample plate is compact, lightweight and/or washable.

In one embodiment, the sample plate comprises a strip or an array format. For example, the sample plate can comprise sample wells arranged in an A×B format, wherein A and B are perpendicular axes. The number of wells along the A axis can be greater than, less than, or equal to the number of wells along the B axis. For example, the number of wells along the A axis or B axis can be 1, 2, 3, 4, 5, 6, 7, 8, 9, 10, 11, 12, 13, 14, 15, 16, 17, 18, 19, 20, 21, 22, 23, or 24. In another embodiment, the number of wells along the A or B axis can be at least 2, 3, 4, 5, 6, 7, 8, 9, 10, 11, 12, 13, 14, 15, 16, 17, 18, 19, 20, 21, 22, 23, or 24. For example, the number of wells can be greater than 10. In one embodiment, the sample plate may comprise a 6×1 strip (6 wells in a single row) or a 9×6 strip (9 wells by 6 wells).

In one embodiment, the sample plate comprises at least one sample well connected to another sample well by a frangible region. The frangible region or connection can allow the sample plate to be easily separated by a user into a plurality of smaller sample plates, such as by snapping or broking the connected sample wells of a sample plate into a plurality of smaller sample plates. For example, a 6×1 strip of sample plates can be snapped into individual 1×1 sample plates comprising a single sample well or into two sample plates each comprising a 3×1 strip of sample wells.

The diameter of a sample well can range from micrometers, millimeters, centimeters or more. For example, the diameter of a sample well can be between 1-100, 100-200, 300-400, 400-500, 500-600, 600-700, 700-800, 800-900, or 900-1000 mm. In one embodiment, the diameter can be less than about 1000 mm, 100 mm, 20 mm, 15 mm, 10 mm or 5 mm. In one embodiment, the size of the sample well is such that the sample plate comprising the sample well can be fitted into a conventional microplate footprint. In one embodiment, one or more of the sample wells have a diameter or maximum width of <1 mm; 1-2 mm; 2-3 mm; 3-4 mm; 4-5 mm; 5-6 mm; 6-7 mm; 7-8 mm; 8-9 mm; 9-10 mm; 10-11 mm; 11-12 mm; 12-13 mm; 13-14 mm; 14-15 mm; 15-16 mm; 16-17 mm; 17-18 mm; 18-19 mm; 19-20 mm; or >20 mm. In one embodiment, the diameter of a sample well is about 12 mm, wherein the cross sectional surface area is 58 mm$^2$ and 54 sample wells of this size is fitted on a sample plate.

The sample well can be of any shape. A sample plate can comprise a plurality of wells in which the sample wells are of the same size and/or same shape. Alternatively, the plurality of wells can comprise a variety of sizes and/or shapes. The well can be circular, oblong, triangular, square, rectangular, pentagonal, hexagonal, septagonal, octagonal, nonagonal, decagonal or polygonal. In one embodiment, the opening of the recess or the cross-section shape of the recess (such as at a location intermediate the opening to the bore and the base of the bore) is circular. In another embodiment, the opening and/or cross-sectional shape of the bore may be substantially circular, elliptical, oblong, triangular, square, rectangular, pentagonal, hexagonal, septagonal, octagonal, nonagonal, decagonal or polygonal.

In one embodiment, a sample plate comprises a plurality of sample wells, wherein one or more of the sample wells comprise one or more central fluid receiving areas and one or more bead receiving chambers. The bead receiving chamber comprises a bead, such as a reagent bead or microsphere, and is also referred to as a bead receiving region or location.

In one embodiment, a subset, or substantially all of the plurality of bead receiving chambers are arranged or configured to receive a single bead or a plurality of beads. Within each sample well a varied number of beads can be inserted, for example if the well has more than one bead receiving chamber. In another embodiment, the sample well comprises at least 2, 3, 4, 5, 6, 7, 8, 9, 10, 11, 12, 13, 14, 15, 16, 17, 18, 19, or 20 bead receiving chambers. In yet another embodiment, one or more wells of a sample plate comprises 2, 3, 4, 5, 6, 7, 8, 9, 10, 11, 12, 13, 14, 15, 16, 17, 18, 19, or 20 bead receiving chambers. In another embodiment, the sample well comprises between 2 and 20 bead receiving chambers. In yet another embodiment, one or more wells of a sample plate comprises 2, 3, 4, 5, 6, 7, 8, 9, 10, 11, 12, 13, 14, 15, 16, 17, 18, 19, or 20 bead receiving chambers.

The bead receiving chamber can be of any shape. A sample well can comprise a plurality of bead receiving chambers in which the bead receiving chambers are of the same size and/or same shape. Alternatively, the plurality of bead receiving chamber can comprise a variety of sizes and/or shapes.

The bead receiving chamber can be circular, oblong, triangular, square, rectangular, pentagonal, hexagonal, septagonal, octagonal, nonagonal, decagonal or polygonal.

A plurality of bead receiving chambers can be arranged circumferentially around a central portion of the sample well; circumferentially around a central bead receiving chamber; in a substantially close-packed manner; in a substantially symmetrical or asymmetrical manner; in a substantially linear or curved manner; in a substantially regular or irregular manner; in an array; and/or in one or more concentric circles with bead receiving chamber.

In one embodiment, the one or more fluid receiving areas is in fluid communication with one or more of the bead receiving chambers. Fluid received in the one or more fluid receiving areas can flow into the one or more bead receiving chambers. For example, in one embodiment, the sample wells comprise one or more central fluid receiving areas and a plurality of bead receiving chambers disposed around the one or more central fluid receiving areas, wherein the one or more central fluid receiving areas are in fluid communication with at least some or all of bead receiving chambers.

In one embodiment, fluid is dispensed into the one or more central fluid receiving areas, which flows into some or all of the bead receiving chambers without overflowing the bead receiving chambers. Fluid can be dispensed directly into the centre of the sample well.

In one embodiment, a bead in the sample plate is such that the bead is flush with the bottom of the well. In one embodiment, the amount of fluid used is the amount used to cover a bead disposed in the base of the sample plate. In one embodiment, the sample plate has a fluid capacity of approximately 800 µl. In another embodiment, the sample plate has a fluid capacity of greater than or less than about 800 µl. However, in some embodiments, less than the fluid capacity, such as about 10, 20, 30, 40, 50, 60, 70, 80, or 90% of the fluid capacity is used in an assay. For example, in one embodiment, about 100, 200, 300, 400, 500, 600, or 700 µl of fluid is used. In one embodiment, approximately 300 µl of fluid is used to cover a bead disposed in the base of a sample plate.

A sample well can comprise an outer circumferential wall, surface or groove wherein fluid dispensed into a sample well is can be confined within the sample well by the outer circumferential wall, surface or groove. In one embodiment, fluid dispensed into the one or more central fluid receiving areas can flows into one or more of the bead receiving chambers without overflowing the outer circumferential wall, surface or groove and/or without overflowing the one or more wall members, surfaces or grooves.

The one or more of the wall members, surfaces or grooves, and optionally, with a portion of the outer circumferential wall, surface or groove, can define an individual bead receiving chamber. The one or more of the wall members, surfaces or grooves can extend inwardly from the outer circumferential wall in a radial, linear or curved manner. Some or all of the wall members, surfaces or grooves can be integral with or depend from the outer circumferential wall. In one embodiment, at least some or all of the wall members, surfaces or grooves are spaced radially from or are separated from the outer circumferential wall by a gap.

The outer circumferential wall, surface or groove can have a height or depth of <1 mm; 1-2 mm; 2-3 mm; 3-4 mm; 4-5 mm; 5-6 mm; 6-7 mm; 7-8 mm; 8-9 mm; 9-10 mm; 10-11 mm; 11-12 mm; 12-13 mm; 13-14 mm; 14-15 mm; 15-16 mm; 16-17 mm; 17-18 mm; 18-19 mm; 19-20 mm; or greater than 20 mm.

A bead retaining chamber can be formed from a base of well and a retention member, membrane, lip or annular portion. A bead or microsphere may be inserted, past or through the retention member, membrane, lip or annular portion into the chamber and may be substantially retained or secured within the chamber by the retention member, membrane, lip or annular portion.

A sample well can comprise an outer circumferential wall together with a plurality of radial wall members which define one or more bead receiving chambers. In one embodiment, a bead in the bead receiving chamber is prevented from passing radially into the central fluid receiving area by the radial wall members. The one or more of the radial wall members can be integral with the outer circumferential wall or are separated from the outer circumferential wall by a gap.

The one or more of the radial wall members can comprise one or more protrusions which confine a bead within a bead receiving chamber and can assist in preventing the bead or microsphere from passing radially into the central fluid receiving area. In one embodiment, the radial wall members have a height or depth of <1 mm; 1-2 mm; 2-3 mm; 3-4 mm; 4-5 mm; 5-6 mm; 6-7 mm; 7-8 mm; 8-9 mm; 9-10 mm; 10-11 mm; 11-12 mm; 12-13 mm; 13-14 mm; 14-15 mm; 15-16 mm; 16-17 mm; 17-18 mm; 18-19 mm; 19-20 mm; or greater than 20 mm.

In one embodiment, fluid which is dispensed into the one or more central fluid receiving areas flows into some or all of the bead receiving chambers without overflowing the outer circumferential wall and/or without overflowing the plurality of radial wall members. Fluid can be dispensed directly into the centre of the sample well.

FIG. 4A shows an individual sample well 14 of a sample plate 11. According to the particular embodiment illustrated in FIG. 4A, the sample well 14 may comprise eight bead receiving chambers 15 disposed around a central fluid receiving area 16. Other embodiments are contemplated wherein a different number of bead receiving chambers or regions 15 are provided. Each bead receiving chamber 15 can be defined by at least two radial wall members 17 together with the outer or inner wall of the sample well 14. The radial wall members 17 can depend from the wall of the sample well 14 and extend towards the centre of the sample well 14. In this embodiment, the wall members 17 do not extend all the way to the centre of the sample well 14 so that a central circular fluid receiving area 16 is provided. At least some or, in some embodiments, all of the radial wall members 17 which terminate adjacent the central fluid receiving area 16 may comprise an enlarged portion which is designed to assist in the retention of beads within their individual bead receiving chambers 15 and to prevent the beads from passing into the fluid receiving area 16. In another embodiment, the height of at least some or substantially all of the radial wall members 17 merely reduces in the region of the central fluid receiving area 16.

In the embodiment shown in FIG. 4A the radial wall members 17 depend from the outer or inner wall of the sample well 14. In another embodiment as illustrated in FIG. 4B the radial wall members 17 do not depend from the wall of the sample well 14. Instead, the radial wall members 17 are spaced apart from the outer or inner wall of the sample well 14. At least some or all of the radial wall members 17 which terminate short of the outer or inner wall of the sample well 14 may comprise an enlarged portion which can be designed to assist in the retention of reagent beads or microspheres within their individual reagent bead or microsphere receiving chambers 15. Other embodiments are contemplated wherein the height of at least some or substantially all of the radial wall members 17 merely reduces towards the outer or inner wall of the sample well 14.

FIG. 4C depicts an embodiment wherein eight different types of reagent beads or microspheres are shown dispensed into separate bead receiving chambers 15 of a sample well. In this embodiment, a first bead 18A is coated with a first reagent, a second bead 18B is coated with a second different reagent, a third bead 18C is coated with a third different reagent, a fourth bead 18D is coated with a fourth different reagent, a fifth bead 18E is coated with a fifth different reagent, sixth bead 18F is coated with a sixth different reagent, a seventh bead 18G is coated with a seventh different reagent and a eighth bead 1811 is coated with an eighth different reagent. In this embodiment, eight individually chosen and distinct probes can be used to detect eight distinct analytes substantially simultaneously on a single fluid sample so that multiplexed testing can be performed.

Figure 5:
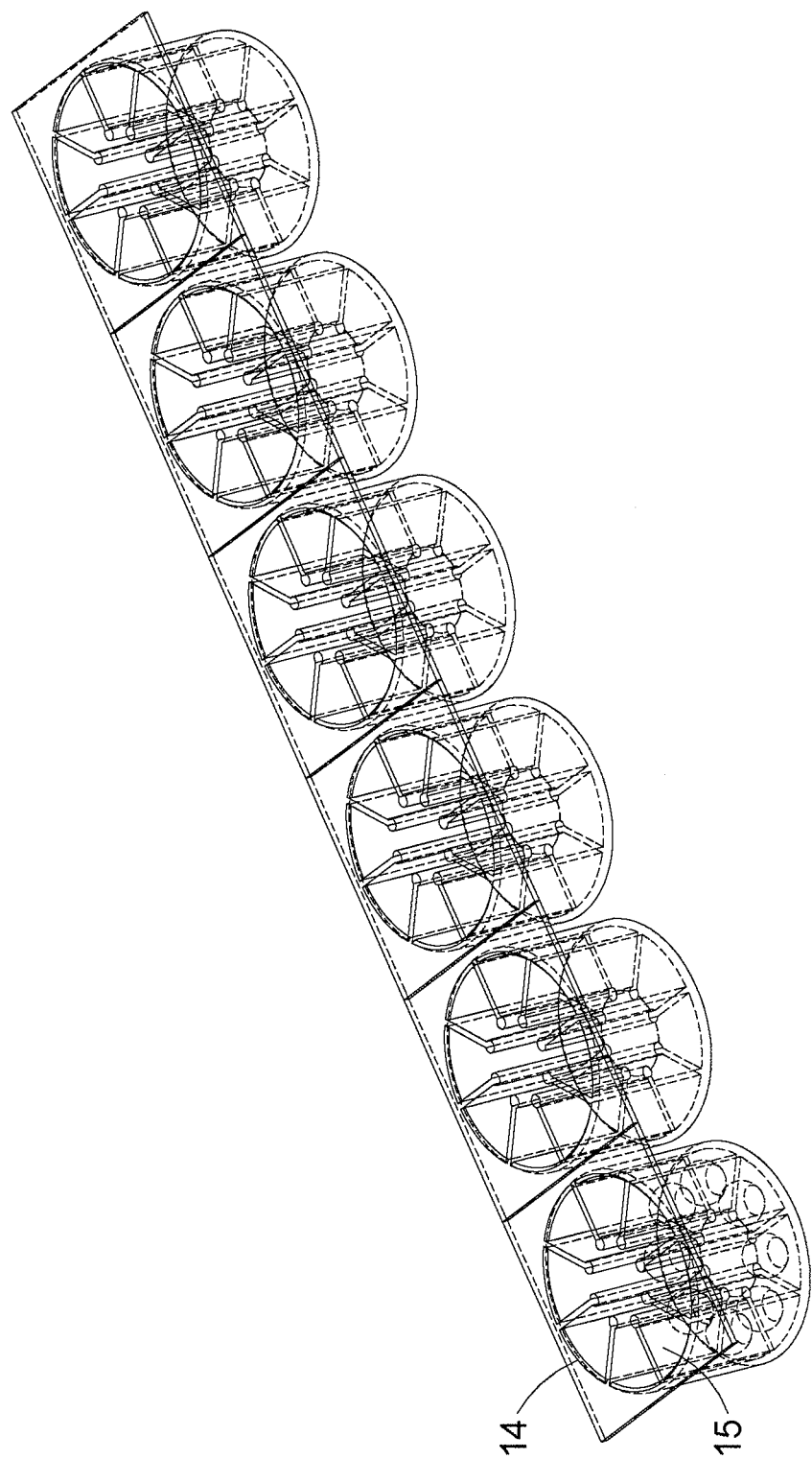
FIG. 5 shows a strip of sample wells according to an embodiment wherein a sample well of a sample plate comprises radial wall members.

FIG. 5 shows another embodiment wherein a sample plate comprising a strip of six sample wells 14 is provided. Each sample well 14 comprises eight bead receiving chambers 15. Although the sample well 14 as depicted in FIGS. 4-5 comprise a plurality of radial or straight walls 17, other embodiments are contemplated wherein the walls separating adjacent reagent bead or microsphere receiving chambers 15 may be curved. In yet another embodiment the bead receiving chamber 15 may have a honeycombed structure formed of a plurality of polygonal (e.g. hexagonal) chambers and/or may comprise a plurality of circular reagent bead or microsphere receiving chambers 15.

A fluid to be tested can be dispensed into the central fluid receiving area 16 of a sample well 14. The fluid may, for example, comprise a sample of blood, serum, saliva or urine taken from a patient. The fluid which is dispensed into the central fluid receiving area 16 of the sample well 14 can flow into each of the adjoining reagent bead or microsphere receiving chambers 15 by flowing between the gap between two radial wall members 17 which help to define a reagent bead or microsphere receiving chamber 15. In one embodiment, the fluid which is dispensed does not flow over the top of the radial wall members 17.

One or more of the beads dispensed into the bead receiving chambers 15 of a sample well 14 may have a ferrous or magnetic layer or coating and/or have a ferrous or magnetic property. A magnetic or electro-static device may be used to attract reagent beads or microspheres as they are being dispensed from a reagent bead or microsphere dispenser 2 (FIG. 1 for example, and further described herein) in order to guide the beads 2 being dispensed into an appropriate reagent bead or microsphere receiving chamber 15 of a sample well 14. Once beads have been dispensed into bead receiving chamber 15 the magnetic or electro-static device may then be used to attract, retain or otherwise hold the beads in their bead receiving chambers 15 for a period of time.

Other embodiments are contemplated wherein a mechanical device or an electrical device may be used to funnel or direct beads into appropriate bead receiving chambers 15 and/or to retain or otherwise hold beads which have been dispensed into bead receiving chambers 15 in their chamber 15 for a period of time.

In a further embodiment, a magnetic, electro-static, mechanical or electrical device may be used to vibrate or agitate bead which have been dispensed into appropriate bead receiving chambers 15. In one embodiment, beads located in bead receiving chambers 15 may be vibrated or agitated once a fluid sample has been dispensed into the central fluid receiving area 16 and once the fluid sample has dispersed into each of the various bead receiving chambers 15. In one embodiment, this process helps to ensure that the various beads are wetted or coated by the dispensed fluid sample. In one embodiment, 10-200 ml of fluid sample may be dispensed into each of the central fluid receiving areas 16 of the sample wells 14 comprising a sample plate 13.

In another embodiment, the bead retaining chamber is a recess, hole, section, bore or pocket. In one embodiment, the sample well comprises a base portion, which comprises one or more recesses. The one or more recesses can comprise a tapered section. The one or more pockets or recesses comprising a tapered section can comprise a bead, such as a reagent bead or microsphere, which is substantially retained or secured within the recess by the tapered section. The bead can be substantially retained or secured at the opening of the recess or at a location intermediate, or at a point between, the opening of the recess and the base of the recess.

In another embodiment, a bead is substantially retained or secured within the recess by an interference or friction fit with the tapered section of the bore. In one embodiment, a preset force compresses the bead and/or deforms the recess, such as the tapered section of the recess, so as to create or enhance the interference or friction fit with the tapered section of the recess. In one embodiment, the bead present in a recess does not touch the bottom of a well. In another embodiment, the bead present or within a recess does not contact the bottom of a well or a base portion of a sample well. In another embodiment, a bead or microsphere forms a substantially fluid-tight seal with the tapered section of the recess. For example, a bead can form a fluid-tight seal with the tapered section of the recess and substantially prevent fluid from flowing from the sample well past the bead. The fluid-tight seal can be at the opening of the recess or at a location intermediate, or at a point between, the opening of the recess and the base of the recess.

In another embodiment, the one or more recesses can comprise a diameter less than a diameter of a bead, such as a reagent bead or microsphere, in which a portion of the bead is substantially retained or secured within the recess. The bead can be substantially retained or secured at the opening of the recess or at a location intermediate, or at a point between, the opening of the recess and the base of the recess.

In another embodiment, a bead is substantially retained or secured within the recess by an interference or friction fit with the circumference of the recess. In one embodiment, a preset force compresses the bead and/or deforms the recess so as to create or enhance the interference or friction fit with the recess. In one embodiment, the bead present in a recess does not touch the bottom of a well. In another embodiment, the bead present or within a recess does not contact the bottom of a well or a base portion of a sample well. In another embodiment, a bead or microsphere forms a substantially fluid-tight seal with the tapered section of the recess. For example, a bead can form a fluid-tight seal with a diameter of the recess and substantially prevent fluid from flowing from the sample well past the bead. The fluid-tight seal can be at the opening of the recess or at a location intermediate, or at a point between, the opening of the recess and the base of the recess.

In one embodiment, a bead is deposited or inserted onto a sample plate having a recess. In one embodiment, a bead is deposited or inserted onto a sample plate having a tapered recess. The tapered section of the sample plate can firmly secure or lock a bead in position once inserted. In another embodiment, a bead is deposited or inserted onto a sample plate having a recess with a diameter less than a diameter of a bead, and the recess can firmly secure or lock a bead in position once inserted.

In one embodiment, a bead is substantially retained or secured within or by a recess when the sample plate (i.e. the plane of the sample plate) is tipped by more than about 10°, 20°, 30°, 40°, 50°, 60°, 70°, 80°, or 90° to horizontal, or is inverted.

In one embodiment, a preset force is used to insert a bead. The sample plate is therefore particularly robust during manufacture and in subsequent processing stages including the stage of inserting a plurality of beads into tapered holes or holes with diameters less than the diameter of the beads and the subsequent handling and processing of the sample plate. In one embodiment, once a bead is inserted into a sample plate, the bead is typically not free to move in any direction and becomes a fixed part of the sample plate. In one embodiment, the angle of the taper is configured such that the bead is locked or is otherwise firmly secured into the holes. In another embodiment, the diameter of the recess is configured such that the bead is locked or is otherwise firmly secured into the holes.

The one or more recesses provided in the base portion can be arranged circumferentially around a central portion of the sample well; circumferentially around one more central pockets or recesses; in a substantially close-packed manner; in a substantially symmetrical or asymmetrical manner; in a substantially linear or curved manner; in a substantially regular or irregular manner; in an array; and/or in one or more concentric circles with no pocket, recess or bore located at the centre of the base portion.

In one embodiment, the sample plate is arranged so that the pockets, recesses or bores for securing reagent beads are not arranged in the central region of the sample well. Such an arrangement can be advantageous in that reagent which coats a bead is not inadvertently washed off the beads by the force of the fluid jet from a wash head or pipette tip. In another embodiment, the sample plate has improved fluid mixing as compared to other sample plates. In one embodiment, the sample wells comprise beads which are pressed or inserted into the pockets or recesses. The recesses can be tapered, have a diameter greater than the diameter of the beads, or both. The tops of the reagent beads once inserted can be flush or level with the bottom of the sample well. Mixing can be performed using fluid that is above the surface of the beads to pull fluid from the pocket area around the bead. Thus, in one embodiment, the bottom of the bead below the press fit line does not come into contact with the fluid. In one embodiment, the bead does not protrude above the bottom of the sample well and are not susceptible to damage through handling, pipetting or washing. However, in another embodiment, one or more of reagent beads may protrude above the bottom of the sample well. In another embodiment, the bead within a recess protrudes from the bottom of a sample well and does not touch the bottom of a well.

The recesses of a sample plate can have different diameters to accommodate different size beads if desired. For example, the tapered bores can have different diameters to accommodate different size beads and recesses can have diameters less than different size beads. The one or more pockets or recesses can also comprise a countersunk or enlarged portion for facilitating the insertion of a reagent bead or microsphere into one or more of the pockets or recesses.

Within each sample well a varied number of beads can be inserted, for example if the well has more than one pocket or recess for a bead. In one embodiment, the sample well comprises at least 2, 3, 4, 5, 6, 7, 8, 9, 10, 11, 12, 13, 14, 15, 16, 17, 18, 19, or 20 pockets or recesses. In yet another embodiment, one or more wells of a sample plate comprises 2, 3, 4, 5, 6, 7, 8, 9, 10, 11, 12, 13, 14, 15, 16, 17, 18, 19, or 20 pockets or recesses. In another embodiment, the sample well comprises between 2 and 20 pockets or recesses. In yet another embodiment, one or more wells of a sample plate comprises 2, 3, 4, 5, 6, 7, 8, 9, 10, 11, 12, 13, 14, 15, 16, 17, 18, 19, or 20 pockets or recesses.

In one embodiment, a sample well comprises 6×3 0 mm diameter pockets or recesses, such as tapered bores or recesses with a diameter less than the diameter of a bead to be added to the sample well. In another embodiment, a sample well comprises 10×2.0 mm diameter pockets or recesses, such as tapered bores or recesses with a diameter less than the diameter of a bead to be added to, or present in, the sample well. In yet another embodiment, a sample well comprises 21×1.75 mm diameter pockets or recesses, such as tapered bores or recesses with a diameter less than the diameter of a bead to be added to, or present in, the sample well.

The central region of the sample well can be kept free of pockets or recesses, such as tapered bores or recesses with a diameter less than the diameter of a bead to be added to, or present in, the sample well. The pockets or recesses, such as tapered bores or recesses with a diameter less than the diameter of a bead to be added to, or present in, the sample well, may be arranged in one or more concentric circles or other patterns about the central region of the sample well.

In one embodiment, a sample plate having an array of 9×6 sample wells may be provided. If 6 pockets or recesses, such as tapered bores or recesses with a diameter less than the diameter of a bead to be added to, or present in, the sample well, are provided per sample well, then the sample plate can accommodate 324 beads per plate. If 10 pockets or recesses, such as tapered bores or recesses with a diameter less than the diameter of a bead to be added to, or present in, the sample well, are provided per sample well, then the sample plate can accommodate 540 beads per plate. If 21 pockets or recesses, such as tapered bores or recesses with a diameter less than the diameter of a bead to be added to, or present in, the sample well, are provided per sample well, then the sample plate can accommodate 1134 beads per plate.

The tapered section can has a taper at least about 1°. In another embodiment, the tapered section has a taper of between 1° and 15°. In yet another embodiment, the tapered section has a taper selected from the group consisting of: 2-4°; 4-6°; 6-8°; and 8-10°. In yet another embodiment, the tapered section is substantially linearly tapered. In one embodiment, the diameter or circumference of the recess varies (e.g. decreases) substantially linearly with the depth of the recess. For example, a recess with a cross-sectional shape that is non-circular, then a cross-sectional dimension (e.g. the smallest span of the cross-sectional shape of the recess) or the perimeter of the cross-sectional shape of the recess varies (e.g. decreases) substantially linearly with the depth of the recess. In another embodiment, a recess with a cross-sectional shape that is circular, then a cross-sectional dimension (e.g. the diameter of the opening of the recess) or the perimeter of the cross-sectional shape of the recess varies (e.g. decreases) substantially linearly with the depth of the recess.

The diameter of the recess, the opening of the recess or cross-sectional of the recess can be greater than, equal to, or less than the diameter of a bead added to the sample plate. In one embodiment, the diameter of the opening of the recess is greater than the diameter of the bead or microsphere. In another embodiment, the recess has an opening that is circular. In yet another embodiment, the opening of the recess has a non-circular cross-sectional shape. In one embodiment, the opening of the recess with a non-circular cross-sectional shape has a span that is smaller, greater, or equal to the diameter of the bead or microsphere.

For example, the diameter of recess can be greater than the diameter of the bead. In one embodiment, the recess comprises a tapered section. In yet another embodiment, recess does not comprise a tapered section. In one embodiment, the diameter of the recess is at least about 5, 10, 15, 20, 35, 30, 35, 40, 45, 50, 55, 60, 65, 70, 75, 80, 85, 90, 95, or 100% greater than the diameter of a bead to be deposited to, or present in, the sample plate. In yet another embodiment, the diameter of the recess is less than the diameter of a bead to be added to, or present in, the sample plate. For example, the recess can not have a tapered section. In one embodiment, the diameter of the recess is at least about 5, 10, 15, 20, 35, 30, 35, 40, 45, 50, 55, 60, 65, 70, 75, 80, 85, 90, 95, or 100% less than the diameter of a bead to be deposited to, or present in, the sample plate.

The diameter of the recess can be <1 mm; 1-2 mm; 2-3 mm; 3-4 mm; 4-5 mm; 5-6 mm; 6-7 mm; 7-8 mm; 8-9 mm; 9-10 mm; 10-11 mm; 11-12 mm; 12-13 mm; 13-14 mm; 14-15 mm; 15-16 mm; 16-17 mm; 17-18 mm; 18-19 mm; 19-20 mm; or greater than 20 mm. The diameter of a recess can range from micrometers, millimeters, centimeters or more. For example, the diameter of a recess can be between 1-100, 100-200, 300-400, 400-500, 500-600, 600-700, 700-800, 800-900, or 900-1000 mm. In one embodiment, the diameter can be less than about 1000 mm, 100 mm, 20 mm, 15 mm, 10 mm or 5 mm. In one embodiment, a recess has a diameter or maximum width of <1 mm; 1-2 mm; 2-3 mm; 3-4 mm; 4-5 mm; 5-6 mm; 6-7 mm; 7-8 mm; 8-9 mm; 9-10 mm; 10-11 mm; 11-12 mm; 12-13 mm; 13-14 mm; 14-15 mm; 15-16 mm; 16-17 mm; 17-18 mm; 18-19 mm; 19-20 mm; or >20 mm. In yet another embodiment, the diameter of the recess is selected from the group consisting of: <0.5 mm; 0.5-1.0 mm; 1.0-1.5 mm; 1.5-2.0 mm; 2.0-2.5 mm; 2.5-3.0 mm; 3.0-3.5 mm; 3.5-4.0 mm; 4.0-4.5 mm; 4.5-5.0 mm; <5.0 mm; and >5.0 mm.

In yet another embodiment, the diameter of the recess at a location intermediate the opening of the recess and the base of the recess (such as a point between the opening of the recess and the base of the recess), is at least about 5% smaller than the diameter of the bead or microsphere. The intermediate location can be at least about 5% smaller than the diameter of the opening of the recess, such as for a tapered section of a recess. In one embodiment, the recess has a non-circular cross-sectional shape and the smallest span of the cross-sectional shape of the recess at a location intermediate the opening of the recess and the base of the recess is at least about 5% smaller than the diameter of the bead or microsphere. In one embodiment, the intermediate location is at least about 5% smaller than the diameter of the non-circular cross-sectional opening.

The diameter of the intermediate location of a recess can be <1 mm; 1-2 mm; 2-3 mm; 3-4 mm; 4-5 mm; 5-6 mm; 6-7 mm; 7-8 mm; 8-9 mm; 9-10 mm; 10-11 mm; 11-12 mm; 12-13 mm; 13-14 mm; 14-15 mm; 15-16 mm; 16-17 mm; 17-18 mm; 18-19 mm; 19-20 mm; or greater than 20 mm. The diameter of the intermediate location of a recess can range from micrometers, millimeters, centimeters or more. For example, the diameter of the intermediate location of a recess can be between 1-100, 100-200, 300-400, 400-500, 500-600, 600-700, 700-800, 800-900, or 900-1000 mm. In one embodiment, the diameter of the intermediate location of a recess can be less than about 1000 mm, 100 mm, 20 mm, 15 mm, 10 mm or 5 mm. In one embodiment, a diameter of the intermediate location of a recess has a maximum width of <1 mm; 1-2 mm; 2-3 mm; 3-4 mm; 4-5 mm; 5-6 mm; 6-7 mm; 7-8 mm; 8-9 mm; 9-10 mm; 10-11 mm; 11-12 mm; 12-13 mm; 13-14 mm; 14-15 mm; 15-16 mm; 16-17 mm; 17-18 mm; 18-19 mm; 19-20 mm; or >20 mm. In yet another embodiment, the diameter of the intermediate location of a recess is selected from the group consisting of: <0.5 mm; 0.5-1.0 mm; 1.0-1.5 mm; 1.5-2.0 mm; 2.0-2.5 mm; 2.5-3.0 mm; 3.0-3.5 mm; 3.5-4.0 mm; 4.0-4.5 mm; 4.5-5.0 mm; <5.0 mm; and >5.0 mm.

In another embodiment, the depth of the recess is can range from micrometers, millimeters, centimeters or more. For example, the depth of the recess can be between 1-100, 100-200, 300-400, 400-500, 500-600, 600-700, 700-800, 800-900, or 900-1000 mm. In one embodiment, the depth of the recess can be less than about 1000 mm, 100 mm, 20 mm, 15 mm, 10 mm or 5 mm. In one embodiment, the depth of the recess has a maximum depth of <1 mm; 1-2 mm; 2-3 mm; 3-4 mm; 4-5 mm; 5-6 mm; 6-7 mm; 7-8 mm; 8-9 mm; 9-10 mm; 10-11 mm; 11-12 mm; 12-13 mm; 13-14 mm; 14-15 mm; 15-16 mm; 16-17 mm; 17-18 mm; 18-19 mm; 19-20 mm; or >20 mm. In yet another embodiment, the depth of the recess is selected from the group consisting of: <0.5 mm; 0.5-1.0 mm; 1.0-1.5 mm; 1.5-2.0 mm; 2.0-2.5 mm; 2.5-3.0 mm; 3.0-3.5 mm; 3.5-4.0 mm; 4.0-4.5 mm; 4.5-5.0 mm; <5.0 mm; and >5.0 mm.

In one embodiment, the depth at which the diameter of the recess becomes less than the diameter of the bead can be equal to or greater than the radius of the bead such that the bead does not protrude above the bottom of the sample well. In one embodiment, the recess has a cross-sectional shape that is circular, and the diameter of the recess is less than the diameter of the bead, which is equal to or greater than the radius of the bead. In another embodiment, the recess has a cross-sectional shape that is non-circular, and the recess depth is the smallest span of the cross-sectional shape of the recess, which is less than the diameter of the bead and is equal to or greater than the radius of the bead.

In one embodiment, the sample plate enables multiple tests to be carried out in a single sample well. In one embodiment, different beads are disposed into separate bores in the same sample well thereby enabling multiplexing to be performed. Beads can be pressed into the tapered holes in the base of the well as desired which results in a high degree of flexibility and the ability to use the entire sample well with a high efficiency. In another embodiment, beads can be pressed into holes in the base of the well, wherein the diameter of the holes is greater than the diameter of the beads, as desired which results in a high degree of flexibility and the ability to use the entire sample well with a high efficiency.

Figure 6:
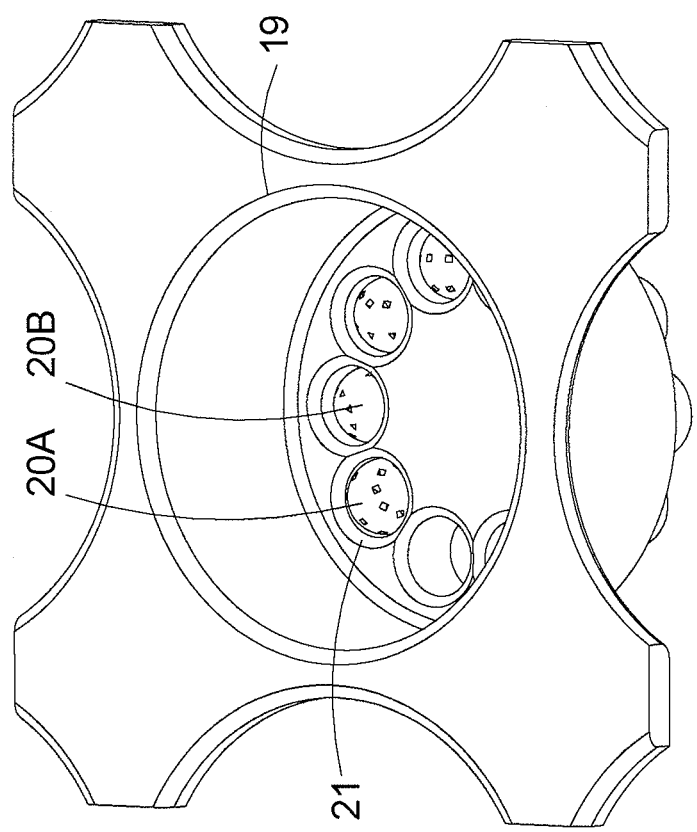
FIG. 6 shows a sample well of a sample plate comprising a plurality of pockets, recesses or bores.

An embodiment of a sample plate with sample wells comprising one or more recesses for a bead retaining member is depicted in FIG. 6. In this embodiment, a sample plate is provided which comprises a plurality of sample wells 19. In one embodiment, the sample plate may comprise a 9×6 array of sample wells 19. A single sample well 19 is shown in FIG. 6. Embodiments are also contemplated wherein the sample plate may comprise a strip of sample wells 19 e.g. the sample plate may comprise, for example, a 1×9 or 1×6 array or strip of sample wells 19.

Each sample well 19 can comprise a plurality of pockets, recesses or bores 21 which are provided in the base of the sample well 19. In the particular embodiment shown in FIG. 6 the sample well 19 comprises ten pockets, recesses or bores 21 which are formed or otherwise provided in the base of a sample well 19. Other embodiments are contemplated wherein a different number of pockets, recesses or bores 21 may be provided in the base of the sample well 19. For example, according to alternative embodiments at least some or all of the sample wells 19 provided in a sample plate may least 2, 3, 4, 5, 6, 7, 8, 9, 10, 11, 12, 13, 14, 15, 16, 17, 18, 19, or 20 pockets, recesses or bores 21.

The pockets, recesses or bores 21 can be provided around the edge or perimeter of the sample well 19 and the centre or central region of the base of the sample well 19 is substantially flat and free from pockets, recesses or bores 21. Thus, in the embodiment depicted in FIGS. 4-5, the sample plate comprised a plurality of radial wall members in order to retain reagent beads or microspheres in their respective reagent bead or microsphere receiving chamber. However, according to the embodiment depicted in FIGS. 6-7, the beads are secured within the pockets, recesses or bores 21 of the sample plate 19 and hence radial wall members are not provided. In yet another embodiment, a combination of the designs of FIGS. 4-5 and FIGS. 6-7 may be combined so that a sample plate is provided comprising a plurality of bead receiving chambers which are in part defined by a plurality of radial wall members. At least some of the bead receiving chambers may further comprise a pocket, recess or bore provided in the base of the reagent bead or microsphere receiving chamber. In this embodiment, reagent beads or microspheres may either be dispensed into a reagent bead or microsphere receiving chamber or the reagent beads or microspheres may be firmly secured in a pocket, recess or bore provided in the base of the reagent bead or microsphere receiving chamber.

Other embodiments are also contemplated wherein a hybrid between a conventional microplate and a sample plate according to the first and/or second main embodiments may be provided. For example, according to an embodiment a sample plate may be provided which comprises one or more conventional sample wells and one or more sample wells having a plurality of recesses, pockets or bores for receiving a reagent bead or microsphere.

Referring to FIG. 6, at least some or all of the pockets, recesses or bores 21 which are provided in the base of a sample well 19 comprise a bore which is tapered along at least a portion or substantially the whole of its length. The pockets, recesses or bores 21 may, for example, be arranged to have a 6° taper. In one embodiment the top (or reagent bead or microsphere receiving portion) of the tapered bore may have a diameter of 1.82 mm. The base of the sample well 19 surrounding the bore may be arranged to have a countersunk portion in order to facilitate the insertion of a reagent bead or microsphere 20A; 20B into the pocket, recess or bore 21. In one embodiment, the outer diameter of the countersunk portion may be 2.25 mm.

Figure 7A:
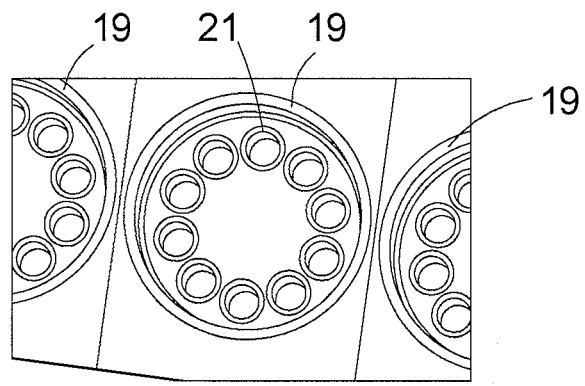
FIG. 7 shows a sample well of a sample plate comprising a plurality of pockets, recesses or bores. A) shows a plan view of a sample well of a sample plate, B) depicts in greater detail the bottom of a sample well, C) shows a reagent bead or microsphere dispensed in a pocket of a sample well.
Figure 7B:
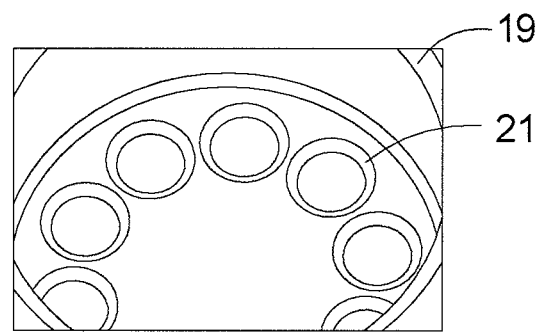

FIG. 7A shows a plan view of a sample well 19 and portions of two adjacent sample wells 19. The sample wells shown in FIG. 7A form part of an array of sample wells 19, which are provided in the sample plate. Each of the sample wells 19 comprise ten pockets, recesses or bores 21, which are disposed in the bottom or base portion of the sample well 19. Beads can be inserted into each of the pockets, recesses or bores 21 of a sample well 19 and the beads secured in the pockets, recesses or bores 21 by virtue of the diameter of the bore tapering and becoming restricted. FIG. 7B shows in greater detail the bottom of a sample well 19 and shows a plurality of pockets, recesses or bores 21 provided in the bottom portion of the sample well 19 each of which are arranged and adapted to receive a reagent bead or microsphere. Each of the pockets, recesses or bores 21 provided in the base of the sample well 19 preferably also comprises a countersunk portion or region at the entrance to each tapered bore. According to a preferred embodiment a single reagent bead or microsphere is dispensed and inserted into each pocket, recess or bore 21.

Figure 7C:
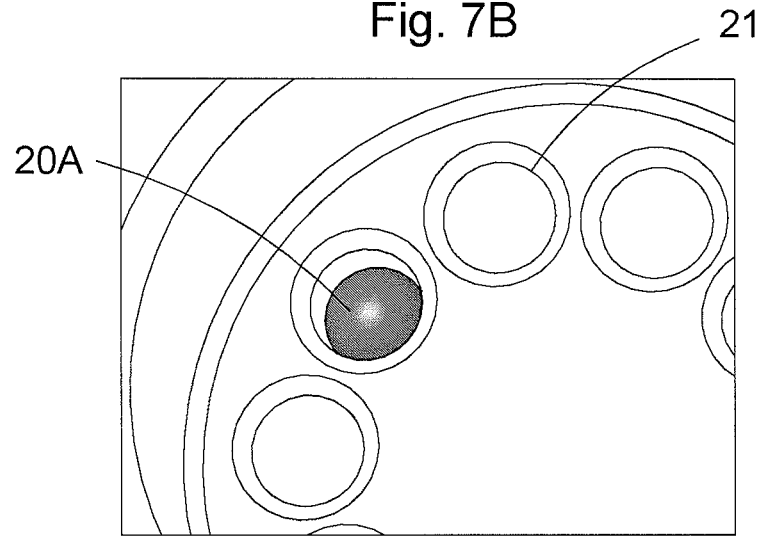

FIG. 7C shows in further detail a bead 20A disposed and securely located in a pocket, recess or bore 21 provided in the base of a sample well 19. The bead 20A is secured within the pocket, recess or bore 21 and the upper surface of the reagent bead or microsphere 20A when secured or located within the pocket, recess or bore 21 is positioned or located approximately 0.3 mm below the surface of the well bottom. For example, in one embodiment, beads 20A located and secured in the pockets, recesses or bores 21 provided in the bottom of a sample well 19 do not project above the entrance to or surface of the pocket, recess or bore 21 and hence do not project above the bottom surface of the sample well 19.

In another embodiment, one or more beads located in one or more pockets, recesses or bores 21 provided in the base of the sample well 19 may be located in relatively shallow pockets, recesses or bores 21 or may be located in one or more pockets, recesses or bores 21 which have a taper such that when the reagent bead 20A is securely positioned within the pocket, recess or bore 21 then the bead projects slightly above the entrance into or surface of the pocket, recess or bore 21 and hence projects above the bottom surface of the sample well 19.

Figures 8A, 8B:
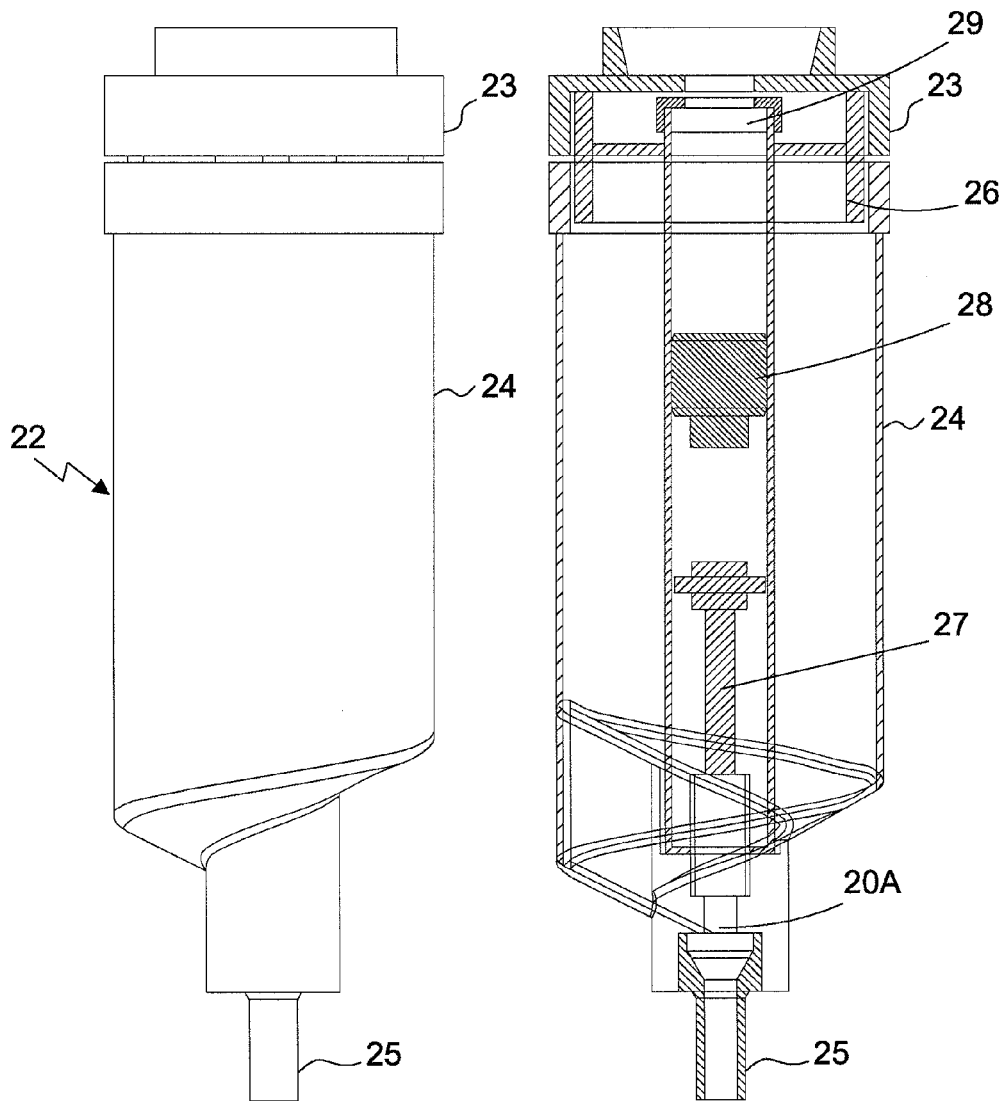
FIG. 8 shows a reagent bead or microsphere dispenser. A) shows a reagent bead or microsphere dispenser, B) shows a cutaway view of the reagent bead or microsphere dispenser.
Figure 9:
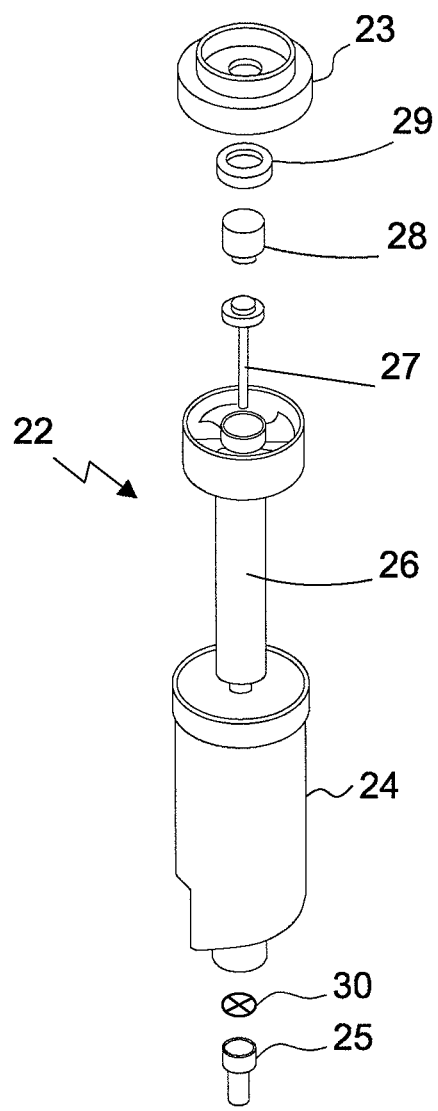
FIG. 9 shows an exploded view of the reagent bead or microsphere dispenser.

Reagent beads or microspheres are can be dispensed into pockets, recesses or bores 21 provided in the bottom of a sample well 19 of a sample plate by means of a bead dispenser, such as depicted in FIGS. 8A, 8B and 9. A bead dispenser 22 as shown in FIG. 8A, comprising an upper cap 23, a syringe body 24 and a barrel 25, which projects from a lower region of the syringe body 24, can be used.

Figure 14A:
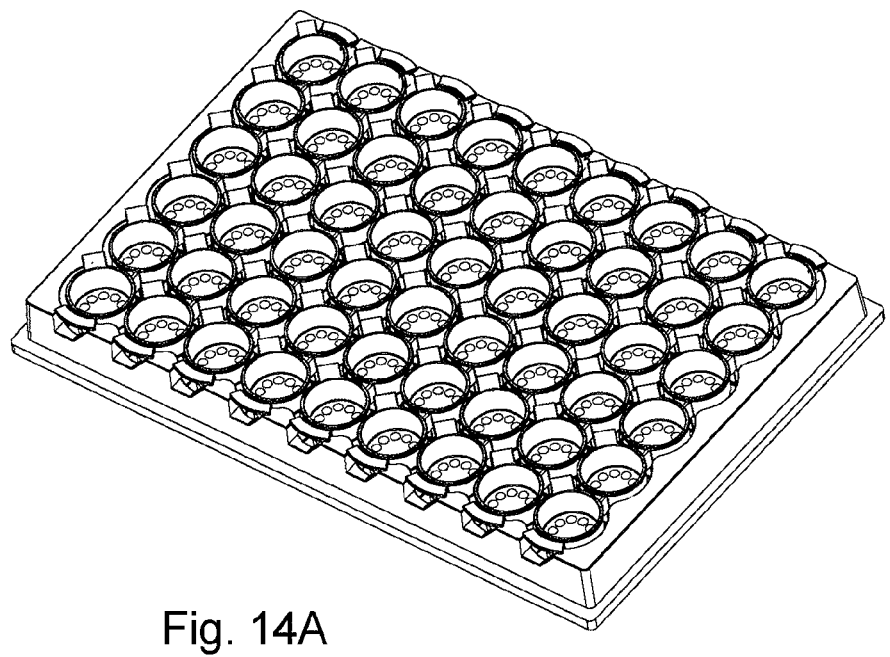
FIG. 14 shows a sample plate and plate frame. A) shows nine sample plates loaded into a plate frame, wherein each sample plate comprises a strip of 6 sample wells and B) shows a plate frame into which sample plate one or more sample plates may be loaded.
Figure 14B:
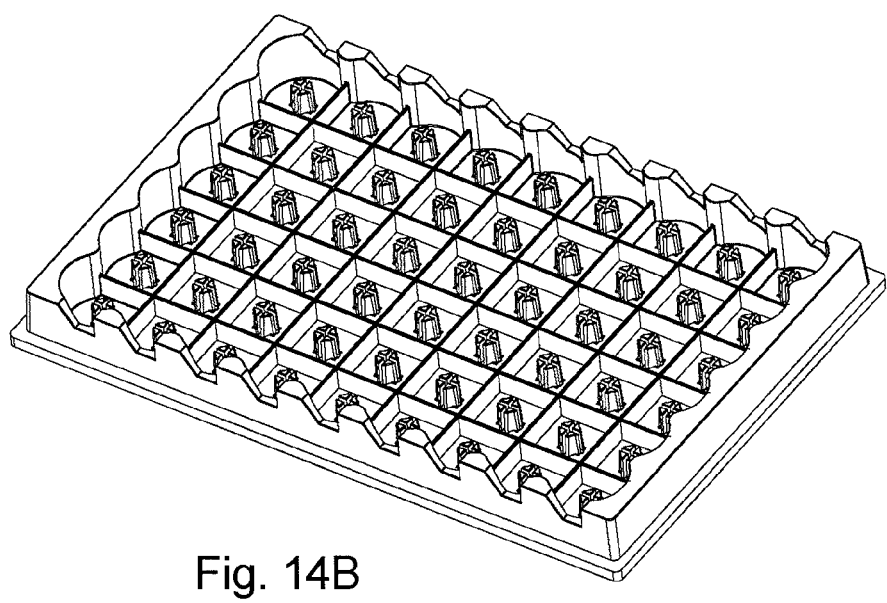

In another aspect of the sample plate, the sample plate can comprises a base comprising a docking portion for securing the sample plate to a corresponding docking portion of a plate frame holder. The sample plate can comprise a male, female or other docking portion for firmly securing the sample plate to the plate frame holder through a corresponding female, male or other docking portion. An embodiment is depicted in FIGS. 14A and 14B. FIG. 14A shows nine sample plates loaded into a plate frame. Each of the sample plates shown in FIG. 14A comprises a 6×1 strip of sample wells. The sample plates can be removeably loaded into the plate frame. Each of the nine sample plates or strips comprises six sample wells and each sample well preferably comprises ten tapered bores which, in use, are arranged to receive a bead. The beads can be loaded into the tapered bores such that the beads do not protrude above the base portion of the sample well. FIG. 14B shows the plate frame into which the sample plates may be loaded in more detail.

Figure 15A:
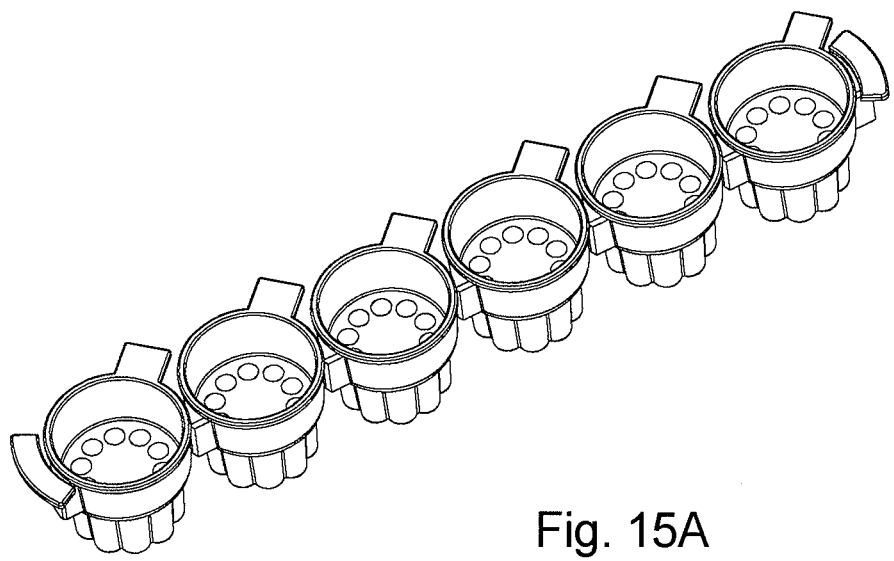
FIG. 15 shows a strip of six sample wells A) in greater detail and B) being loaded into a plate frame.
Figure 15B:
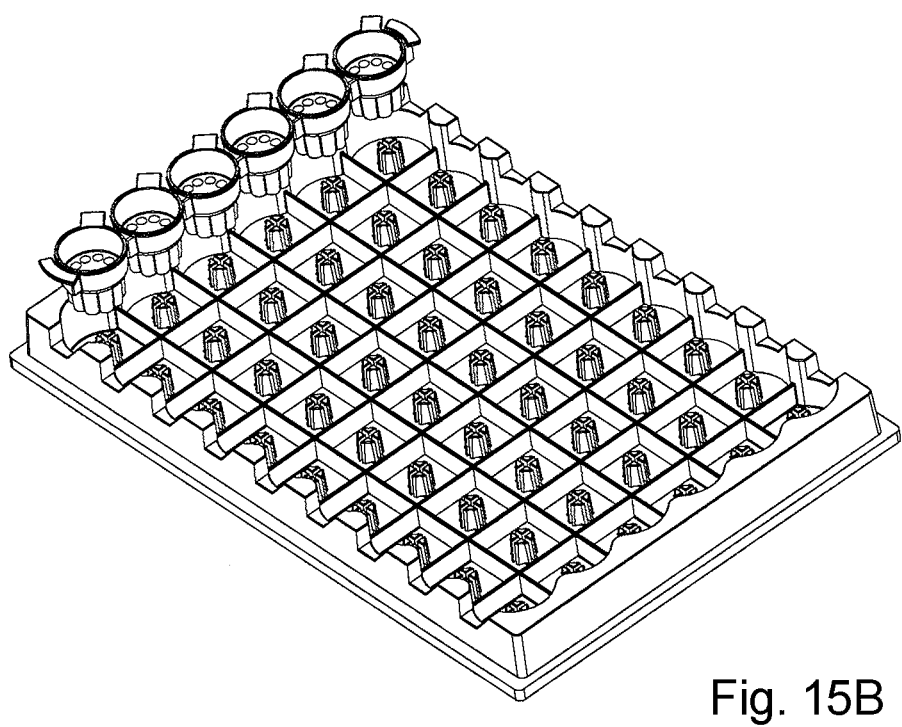

FIG. 15A shows in greater detail a strip of six sample wells. In this embodiment, the sample wells in a strip can be separated or otherwise broken apart. The sample plate or strip can be separated or divided up into single sample wells. FIG. 15B shows a strip of six sample wells being loaded into a plate frame.

Figure 16A:
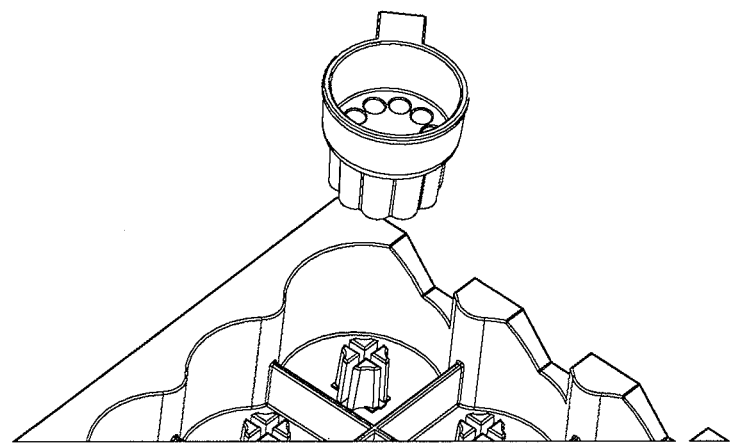
FIG. 16 shows different features of a well. A) shows a single well being loaded into a plate frame. B) shows in greater detail two sample wells connected by a break apart feature. C) shows a sample well having an end feature. D) shows a sample well having an ID and orientation tab.

FIG. 16A shows a single sample well (which has been separated from a strip of sample wells) being loaded into a plate frame. The sample wells can comprise a female portion which is arranged to engage or interlock with a male portion which can be provided on the base of the plate frame. The sample plate or sample strip can be arranged to be finely secured and fixed to the plate frame when loaded onto the plate frame.

Figure 16B:
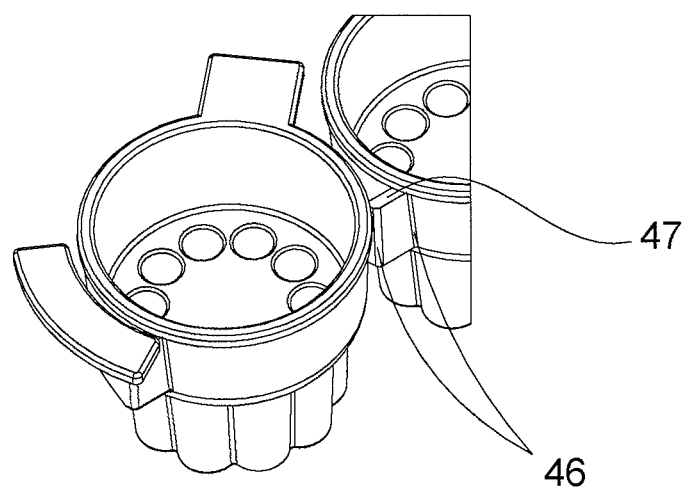

FIG. 16B shows in greater detail two sample wells which are connected by a break-apart feature 47. The break-apart feature 47 allows a user to separate adjacent sample wells. The sample wells may be separated from each other but may still be placed next to each other on the plate frame without interfering with each other. The break-apart feature 47 can comprise one, two or more than two break points 46. In one embodiment, the connecting piece 47 between two sample wells may be separated from a sample well at a first break point 46. The connecting piece 47 may then be broken off or otherwise removed from the single sample well that it is attached to by breaking the connecting piece 47 from the sample well at a second break point 46.

Figure 16C:
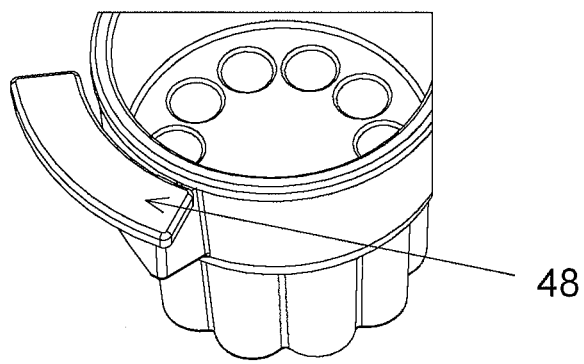

FIG. 16C shows a sample well having an end break-apart feature 48. The end break-apart feature 48 allows the end wells to be used singly in the plate frame without interfering with another sample well. The end break-apart feature 48 provides something for a user to hold in order to remove a strip of sample wells or a single sample well from the plate frame.

Figure 16D:
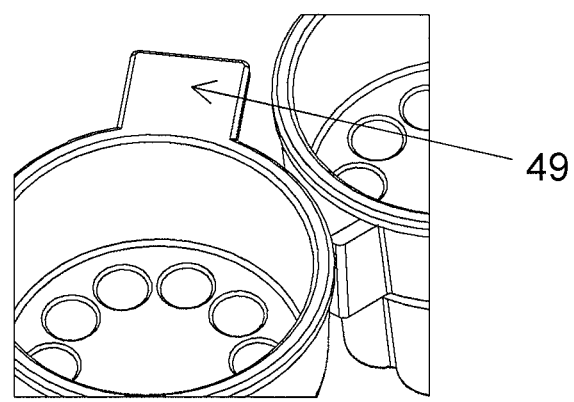

FIG. 16D shows a sample well having an ID and orientation tab 49. The tab 49 allows an identifier to be printed onto the tab 49 or to be otherwise attached to the tab 49. The identifier may comprise a 2D or 3D barcode and/or human readable text. The tab 49 preferably assists a user to orientate a sample well when a single sample well is used by aligning with features in the plate frame and/or on other sample wells.

Figure 17A:
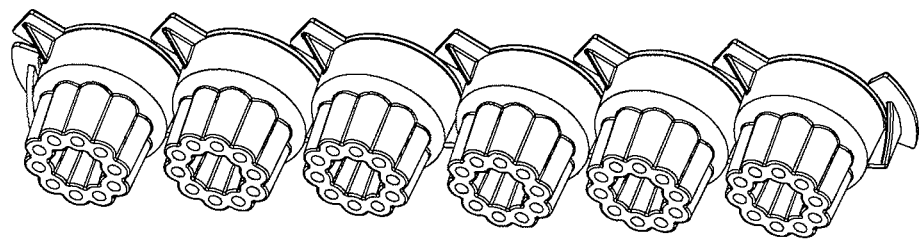
FIG. 17 shows the underneath of a sample well and fitting of a well to a plate frame. A) shows the underneath of a strip of sample wells. B) shows a female alignment and retaining feature which aids in aligning a strip of sample wells with a plate frame. C) shows a corresponding male alignment and retaining feature which is provided in the base of the plate frame.
Figure 17B:
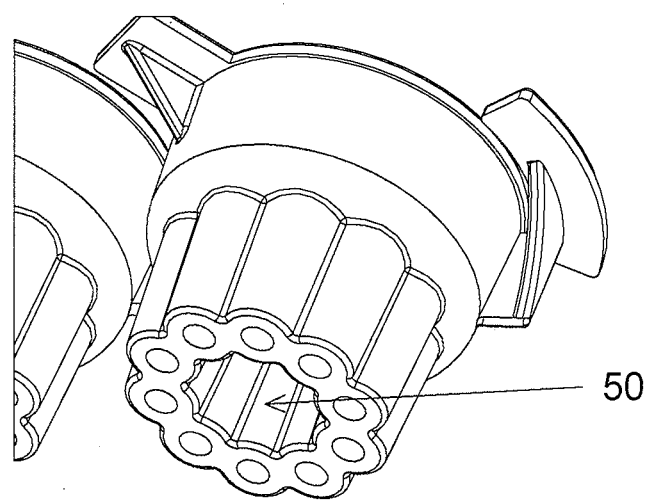
Figure 17C:
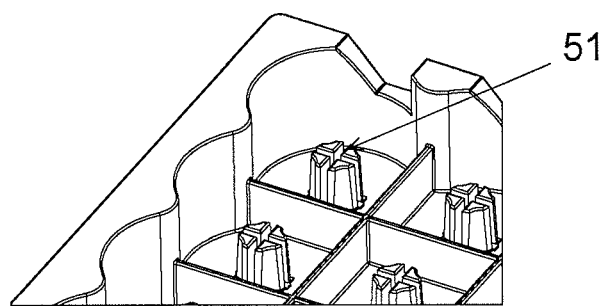

FIG. 17A shows the underneath of a strip of sample wells and shows each sample well comprising ten bores or recesses in which a bead can be inserted. The base or underside of each sample well can also comprise a female portion which is arranged to be mated, in use, with a male portion which is provided in the base of the plate frame. FIG. 17B shows in greater detail a female alignment and retaining feature 50 which can align a strip of sample wells with a plate frame. FIG. 17C shows a corresponding male alignment and retaining feature 51 which is provided in the base of the plate frame. The male portion 51 may comprise a plurality of flexible projections which are preferably deformed inwards as a sample well is located over the male portion 51. The projections on the plate frame can move or close together ensuring that the sample well is kept in place without having to apply undue force either to mount or fix a sample well onto the plate frame and/or to demount a sample well from the plate frame.

Figure 18:
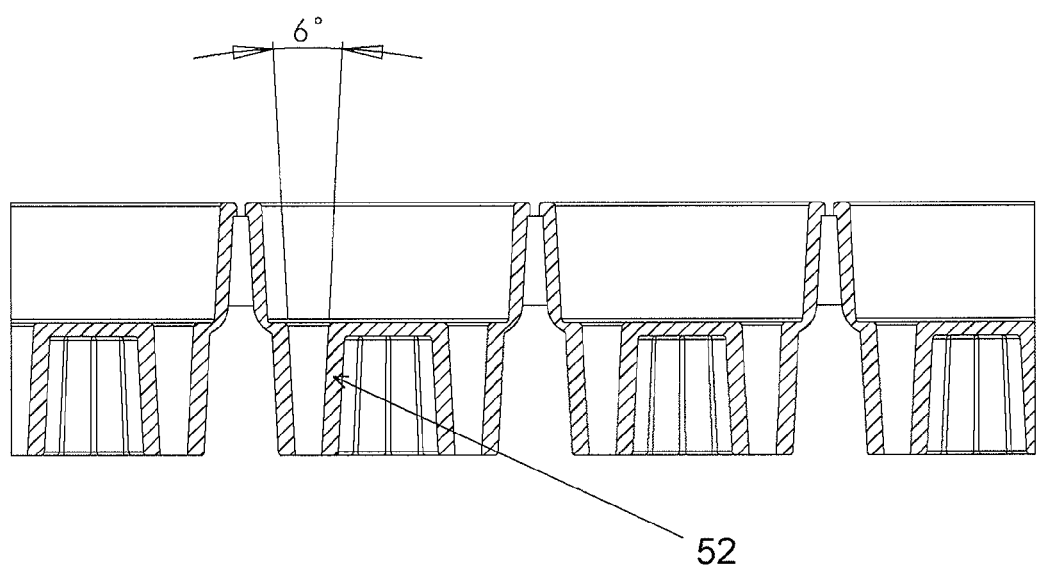
FIG. 18 shows a cross-sectional view of a strip of sample wells and shows t the sample wells having a plurality of tapered bores wherein the angle of the taper is 6.0°.

FIG. 18 shows a cross-sectional view of a strip of sample wells and shows that according to a preferred embodiment the sample wells preferably have a plurality of tapered bores 52. The tapered bores 52 preferably act as pockets into which a reagent bead may be inserted in use. The angle of the taper is preferably 6.0°.

Beads

The sample plate disclosed herein can comprise one or more beads. The bead can be a microparticle, particle, microsphere, or grammatical equivalents. The bead composition is dependent on the type of assay being performed. The bead may be composed of plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles, Teflon or any combination thereof. In one embodiment, a bead, such as present in a bead receiving chambers comprises polystyrene, plastic, a polymer, or a combination thereof. In another embodiment, a bead comprises a ferrous or magnetic coating or has a ferrous or magnetic property. In yet another embodiment, a bead comprises an anti-static coating or has an anti-static property. The bead used in the sample plate reagent beads can be translucent, slightly translucent, or opaque. Commercially available beads can also be used.

The beads need not be spherical and may be of irregular shape. In addition, the beads may be porous. The bead size may range from nanometers to millimeters. The bead may have a diameter of at least 0.1 mm. The bead may have a diameter of between 0.1 mm and 10 mm. In one embodiment, the bead may have a diameter of greater than about 0.5 mm; 0.5-1.0 mm; 1.0-1.5 mm; 1.5-2.0 mm; 2.0-2.5 mm; 2.5-3.0 mm; 3.0-3.5 mm; 3.5-4.0 mm; 4.0-4.5 mm; 4.5-5.0 mm; or greater than about 5.0 mm. The bead may have a diameter greater than, equal to, or less than the diameter of a recess, pocket, or bore of a sample well. For example, the bead may have a diameter less than the diameter of a recess, pocket, or bore of a sample well, wherein the recess, pocket or bore comprises a tapered section. In yet another embodiment, the bead may have a diameter greater than the diameter of a recess, pocket, or bore of a sample well. For example, the recess, pocket, or bore may not comprise a tapered section. The diameter of a bead to be deposited, or present, in the sample plate, can be at least about 5, 10, 15, 20, 35, 30, 35, 40, 45, 50, 55, 60, 65, 70, 75, 80, 85, 90, 95, or 100% greater than the diameter of a recess of the sample plate. In one embodiment, the bead present in a sample plate does not touch the bottom of a sample plate, such as a base portion of a sample well.

A bead within the sample plate may comprise a reagent or probe, or be coated with a reagent or probe. The reagent or probe can be used to analyze a sample, such as by detecting an analyte. The probe or reagent can be attached to the bead. The attachment can be a covalent or non-covalent interaction. The probe can be a nucleic acid, antibody, antibody fragment, protein, peptide, aptamer, or chemical compound. For example, the probe can be an oligonucleotide. In one embodiment, the probe can be used to detect an analyte in a biological sample. In yet another embodiment, the probe can be used to for drug screening. For example, a library of compounds or antibodies can be screened for its binding ability to a protein or nucleic acid probe.

The probe can be used to provide detect a biomarker for a diagnosis or prognosis of a disease or condition, drug response or potential drug response, or for monitoring the progression of a disease or condition. For example, the probe can be an antibody or fragment thereof that is used to detect an antigen that is a biomarker for cancer. In another embodiment, the probe can be an antigen, peptide or protein, which is used to detect an antibody in a sample, which can be an indicative of a disease or condition.

The sample plate disclosed herein can comprise a plurality of probes, wherein a subset of said plurality differs from another subset of said plurality. The plurality of probes can be attached to beads. The different probes can be used to detect different analytes, thus allowing multiplexing with the sample plates disclosed herein. The sample plate can comprise at least 2, 3, 4, 5, 6, 7, 8, 9, 10, 11, 12, 13, 14, 15, 16, 17, 18, 19, or 20 different probes. The probes can be of the same type (for example, different antibodies) or of a different type (for example, a combination of nucleic acid probe(s) and antigen(s)).

Bead Dispensers

Also provided herein is a bead dispensing system comprising a sample plate as disclosed herein and a bead dispenser. The bead dispenser can comprise one or more beads, such as a plurality of beads. In one embodiment, the sample plate is sample to a sample plate comprising one or more sample wells, wherein one or more of the sample wells comprise a bead retaining chamber. In one embodiment, the sample plate comprises a sample well with a base portion comprising one or more recesses.

The recess can comprise a tapered section. In one embodiment, a bore or recess with a tapered section comprises a bead coated or attached with a probe. In another embodiment, the recess comprises a diameter less than the diameter of the bead. The recess can comprise a bead coated or attached with a probe and the diameter of the bead is greater than the diameter of the recess. In one embodiment, the bead present in a recess does not touch the bottom of a well. In another embodiment, the bead present or within a recess does not contact the bottom of a well or a base portion of a sample well.

In yet another embodiment, the system further comprises a control system configured to control dispensing of a plurality of beads from the bead dispenser into one or more sample wells of the sample plate. In one embodiment the bead dispensing system comprises a plurality of bead dispensers.

In one embodiment, the bead dispenser comprises: a syringe body comprising an annular chamber surrounding a longitudinal bore, wherein said annular chamber is configured to channel a bead within said annular chamber towards a chamber provided in said bore; a plunger provided within said longitudinal bore; and a barrel or nozzle, wherein the plunger is configured to dispense a bead from the chamber into the barrel or nozzle. In one embodiment, the bead dispensing system is automatic.

In one aspect, the control system comprises a computer program that causes the control system to control the dispensing of one or more beads or microspheres from the one or more bead or microsphere dispensers into one or more sample wells of a sample plate having one or more pockets or recesses. In one embodiment, the one or more pockets or recesses comprise a tapered section. In another embodiment, the one or more pockets or recesses comprise a diameter less than the diameter of the one or more beads or microspheres.

Also provided herein is a computer readable medium comprising computer executable instructions stored on the computer readable medium, the instructions being arranged to be executable by a control system of the bead dispensing system disclosed herein. The computer readable medium can be a ROM; an EAROM; an EPROM; an EEPROM; a flash memory; an optical disk; a RAM; or a hard disk drive.

The bead dispensing system can further comprise a magnetic device and/or an electro-static device which is configured to attract one or more beads as the beads are being dispensed so that the one or more beads are received in the bead retaining chamber, such as the plurality of pockets, recesses, bores; and/or to attract and/or hold one or more beads which have been dispensed in the bead receiving chambers, such as the plurality of pockets, recesses, bores, so that the one or more beads are held or retained in the bead receiving chambers, such as the plurality of pockets, recesses, bores for a period of time.

In yet another embodiment, the bead dispensing system can further comprise a mechanical device and/or an electrical device which is configured to guide one or more beads as the beads are being dispensed so that the one or more beads are received in the plurality of bead receiving chambers; and/or to retain one or more beads which have been dispensed in the plurality of bead receiving chambers so that the one or more beads are held or retained in the reagent receiving chambers for a period of time.

The bead dispensing system can also further comprise a magnetic device and/or an electro-static device which is configured to vibrate and/or agitate one or more beads which have been received in the plurality of reagent bead or microsphere receiving chambers.

The bead dispensing system can also further comprise a mechanical device and/or an electrical device which is arranged and adapted to vibrate and/or agitate one or more beads, which have been received in the plurality of bead receiving chambers.

In one embodiment, the bead dispenser of the bead dispensing system comprises a tube containing a plurality of beads. In one embodiment, a bead dispenser comprises a helical screw, an auger or a bead transmission device for passing or transmitting one or more beads contained within the bead dispenser to a dispensing region, dispensing end or dispensing tip of the reagent bead or microsphere dispenser.

In one embodiment, the bead dispensing system comprises one or more sensors for sensing whether or not one or more beads have been dispensed from a bead dispenser.

The bead dispensing system can also comprise a translation stage for moving the sample plate relative to one or more bead dispensers. The control system can be configured to control the translation stage so that one or more beads from a bead dispenser are dispensed sequentially into different bead receiving chambers by moving the sample plate relative to the bead dispenser.

In one embodiment, the bead dispensing system comprises a rotatable carousel, wherein the one or more bead dispensers are attached or are attachable to the carousel. The control system can be configured to rotate the carousel after all desired first beads have been dispensed from a first bead dispenser into a plurality of different bead receiving chambers (such as pockets, recesses or bores) of the sample plate so that a second different bead dispenser is then brought into a position wherein the second bead dispenser can then dispense second beads (comprising for example, probes that differs from those attached to said first beads) into a plurality of different bead receiving chambers (such as pockets, recesses or bores) of the sample plate. This process can be repeated for further (e.g. third, fourth, fifth, sixth, seventh, eighth etc.) bead dispensers.

In another embodiment, the bead dispensing system further comprises a fluid dispensing device for dispensing fluid into one or more of the fluid receiving areas of one or more sample wells. The fluid dispensing device can be configured to dispense a predetermined amount of fluid into one or more fluid receiving areas of one or more sample wells. The predetermined amount can range from microliters to milliliters. For example, the fluid dispensing device can be configured to dispense from 1.1.1 to 250 ml into a well, such as less than 1 mL, less than 0.5 mL, less than 300 µl, less than 200 µl, or less than 100 µl. In another embodiment, the fluid dispensing device can be configured to dispense<10; 10-20; 20-30; 30-40; 40-50; 50-60; 60-70; 70-80; 80-90; 90-100; 100-110; 110-120; 120-130; 130-140; 140-150; 150-160; 160-170; 170-180; 180-190; 190-200; and >200 mL. In another embodiment, the fluid dispensing device can be configured to dispense<10; 10-20; 20-30; 30-40; 40-50; 50-60; 60-70; 70-80; 80-90; 90-100; 100-110; 110-120; 120-130; 130-140; 140-150; 150-160; 160-170; 170-180; 180-190; 190-200; and >200 µl.

In another embodiment, the fluid dispensing device can be configured to dispense the fluid at a predetermined rate. For example, the predetermined amount of fluid can be dispensed in less than about 0.5, 1, 2, 3, 4, 5, 6, 7, 8, 9, 10, 15, 30, 45, 60, 90, 120, or 180 seconds. In yet another embodiment, the fluid can be dispensed into a plurality of fluid receiving areas, in which the time between dispensing of a fluid from one fluid receiving area to another is less than about 0.5, 1, 2, 3, 4, 5, 6, 7, 8, 9, 10, 15, 30, 45, 60, 90, 120, or 180 seconds.

In another embodiment, the bead dispensing system further comprises an image analysis device or camera for determining whether or not a bead has been dispensed or is otherwise present in a bead receiving chamber. In one embodiment, the sample plate has a first color and the beads have a second different color which contrasts with the first color in order to facilitate visual detection of the presence or absence of a bead in a bead receiving chamber. In one embodiment, the sample plate may further comprise a luminescence or fluorescence marker.

In another embodiment, the bead dispensing system further comprises a luminescence or fluorescence detecting device for determining whether or not a bead has been dispensed or is otherwise present in a bead receiving chamber by determining whether or not a bead obstructs or partially obstructs the luminescence or fluorescence marker.

In another embodiment, the bead dispensing system further comprises a magnetic and/or electrical and/or capacitive and/or mechanical sensor for sensing whether or not a bead has been dispensed or is otherwise present in a bead receiving chamber of a sample plate.

The control system of the bead dispensing system can determine the number of beads present, the number of beads absent, the number of beads dispensed and/or the number of beads desired to be dispensed in a sample well. The control system may also be able to measure and/or adjusts the volume of fluid dispensed or desired to be dispensed into a sample well dependent upon the number of beads determined to be present, absent, dispensed and/or desired to be dispensed in the sample well. The control system can be configured to ensure that at least some or substantially all beads in a sample well are at least partially or fully immersed by a fluid when the fluid is dispensed into the sample well. The control system can also be configured to ensure that the height of fluid dispensed into a sample well remains substantially constant irrespective of the number of beads present, absent, dispensed or desired to be dispensed into the sample well.

Also provided herein is a method of using a bead dispensing system disclosed herein. In one embodiment, the method comprises providing one or more bead dispensers; providing a sample plate comprising a plurality of sample wells, wherein one or more of the sample wells comprise one or more central fluid receiving areas and a plurality of bead receiving chambers disposed around the one or more central fluid receiving areas, wherein the one or more central fluid receiving areas are in fluid communication with at least some or all of the bead receiving chambers; and controlling the dispensing of beads or microspheres from the one or more bead dispensers into one or more of the plurality of bead receiving chambers. In another embodiment, the method of dispensing beads comprises providing a bead dispenser comprising one or more beads; providing a sample plate comprising one or more sample wells, wherein one or more of the sample wells comprises a base portion; wherein the base portion comprises one or more recesses, and the one or more recesses comprises a tapered section or a diameter that is less than the diameter of the one or more beads; and controlling the dispensing of one or more beads from the bead dispenser into one or more of the sample wells.

One embodiment is depicted in FIG. 1. A rotatable carousel 1 comprising a plurality of docking portions or sections disposed around the outer circumference or perimeter of the carousel 1 is provided with twenty-four docking portions. In other embodiments 1, 2, 3, 4, 5, 6, 7, 8, 9, 10, 11, 12, 13, 14, 15, 16, 17, 18, 19, 20, 21, 22, 23, 25, 26, 27, 28, 29, 30 or >30 docking portions may be provided. A plurality of reagent bead or microsphere dispensers 2 can be attached or are otherwise secured in use to the carousel 1 at some or all of the docking portions. Each docking portion can comprise an upper clip 3 and a lower retaining pin 4. The upper clip 3 and lower retaining pin 4 can be used to secure a bead dispenser 2 to the docking portion. Other embodiments include a retaining pin 4 in an upper position and the clip 3 may be provided in a lower position.

Figure 2:
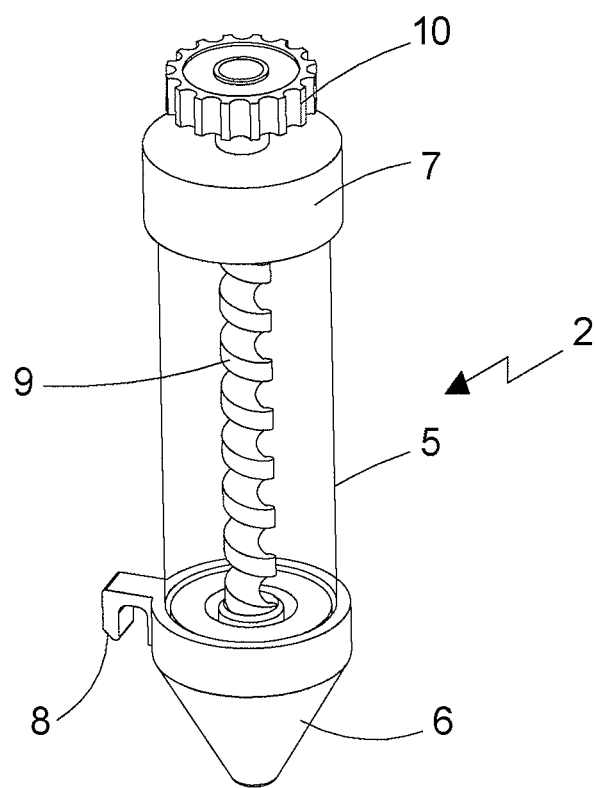
FIG. 2 shows a reagent bead or microsphere dispenser according to the first main embodiment of the present invention.

A single bead dispenser 2 is shown in greater detail in FIG. 2. The bead dispenser 2 can comprise a tubular body 5 having a lower funnel-shaped dispensing portion 6 and an upper cap portion 7. Each bead dispenser 2 can be filled with a plurality of beads. In one embodiment, about 2000 beads, each having a diameter of about 1.75 mm, can be loaded into a single bead dispenser 2. The capacity of the bead dispenser 2 may be greater or smaller. For example, the capacity of a single bead dispenser can be about 500, 1000, 1500, 2000, 2500, 3000, 3500, 4000, 4500, 5000, 5500, or 6000 beads. In yet another embodiment, the capacity of a single bead dispenser can be at least 500, 1000, 1500, 2000, 2500, 3000, 3500, 4000, 4500, 5000, 5500, or 6000 beads.

According to another embodiment, the reagent bead or microsphere dispensers 2 may be arranged to handle reagent beads or microspheres having a diameter other than 1.75 mm. Other embodiments are also contemplated wherein reagent beads or microspheres in a first reagent bead or microsphere dispenser 2 may have a first diameter and wherein reagent beads or microspheres in a second different reagent bead or microsphere dispenser 2 may have a second different diameter. Still other embodiments are also contemplated wherein the reagent beads or microspheres loaded into a particular reagent bead or microsphere dispenser 2 may have a plurality or mixture of different diameters.

In one embodiment, one or more of the bead dispensers 2 comprises a hook 8 which depends from the funnel-shaped dispensing portion 6 and is arranged to connect or lock with the retaining pin 4 of a docking portion on the carousel 1. An upper portion of the tubular body 5 can be arranged to be secured to the docking portion by the clip 3 of the docking portion. The upper clip 3 of at least some of the docking portions may take a different form to that shown in FIG. 1. Other embodiments are contemplated wherein different ways of securing bead dispensers 2 to docking portions of the carousel 1 can also be used.

In one embodiment, each bead dispenser, or a subset of bead dispensers, 2 comprises a central auger, helical screw or screw thread mechanism 9 which when rotated translates beads from within the tubular body 5 towards the dispensing portion 6. The base of the tubular body 5 which holds beads can comprise an annular disk or base section having a central aperture. The auger, helical screw or screw thread mechanism 9 can pass through the central aperture in the base of the tubular body 5. The dispensing portion 6 can comprise a tubular bore through which the auger, helical screw or screw thread mechanism 9 passes. The diameter of the tubular bore within the dispensing portion 6 and the pitch of the auger, helical screw or screw thread mechanism 9 can be configured such that beads within the dispensing portion 6 are advanced towards the nozzle of the dispensing portion 6 and may be dispensed one at a time from the dispensing portion 6.

A shaft or upper end of the auger, helical screw or screw thread mechanism 9 can be connected to a first cog or other first drive mechanism 10. With reference to FIG. 1, the first cog or first drive mechanism 10 at the upper end of the auger, helical screw or screw thread mechanism 9 can be configured to be driven by a corresponding second drive cog 11 or a second drive mechanism which is configured on an arm 12 of the carousel 1. Teeth on the first cog 10 of the bead dispenser 2 can engage and interlock with corresponding teeth on the second drive cog 11 of the arm 12 of the carousel 1 so that rotation of the second drive cog 11 on the arm 12 of the carousel 1 causes rotation of the first cog 10 and hence rotation of the auger, helical screw or screw thread mechanism 9 which is connected to the first cog 10.

In one embodiment, each bead dispenser, or a subset of a plurality of bead dispensers, 2 is filled with a plurality of beads. The beads can comprise a polystyrene, plastic or polymer core which is coated with a ferrous or magnetic coating or have a ferrous or magnetic property. The beads may be coated with a reagent or probe (e.g. an antibody or antigen) which is used to analyze or detect one or more samples. In one embodiment, the reagent or probe may be used to analyze samples by polymerase chain reactions (PCR) or as part of an immunoassay procedure. For example, the reagent or probe can be a nucleic acid or oligonucleotide. In another embodiment, the reagent or probe may comprise a nucleic acid sequence, such as a DNA or RNA sequence, which is used as a hybridization probe to detect the presence of complementary DNA or RNA sequences in a sample. The beads may also be coated with an anti-static coating or may have an anti-static property.

In another embodiment, one or more sensors may be configured on the carousel 1 below or close to the dispensing portion 6 or a bead dispenser 2. The one or more sensors can monitor whether or not one or more beads have been dispensed from the dispensing portion 6 into a bead receiving chamber of a sample plate 13. In one embodiment, the pitch of the auger, helical screw or screw thread mechanism 9 and the speed of rotation of the auger, helical screw or screw thread mechanism 9 is such that individual beads can be dispensed from the dispensing portion 6 of a bead dispenser 2 in less than 0.5 seconds. In another embodiment, the bead dispenser can be configured to dispense the beads at a predetermined rate. For example, the beads can be dispensed in less than about 0.5, 1, 2, 3, 4, 5, 6, 7, 8, 9, 10, 15, 30, 45, 60, 90, 120, or 180 seconds. In yet another embodiment, the beads can be dispensed into a bead receiving chamber, in which the time between dispensing of a first bead and a second bead is less than about 0.5, 1, 2, 3, 4, 5, 6, 7, 8, 9, 10, 15, 30, 45, 60, 90, 120, or 180 seconds.

As is shown in FIG. 1, a sample plate 13 can be mounted on a translation stage below the arm 12 of the carousel 1. The sample plate 13 can comprise a plurality of sample wells. Each sample well can comprise a central fluid receiving area and a plurality of bead receiving chambers disposed around the central fluid receiving area. In one embodiment, beads from a bead dispenser 2 are dispensed into bead receiving chambers in the sample plate 13. The sample plate 13 can be translated by the translation stage so that a desired bead receiving chamber is located in close proximity to the nozzle of the dispensing portion 6 of the bead dispenser 2. A bead can then be dispensed into a bead receiving chamber and the sample plate 13 is moved by the translation stage so that a different bead receiving chamber is disposed in close proximity to the nozzle of the bead dispenser 2. The process of dispensing a bead and translating the sample plate 13 can be repeated and/or automated. Once all desired beads from a particular bead dispenser 2 have been dispensed into appropriate bead chambers of the sample plate 13, the carousel 1 is can be rotated in order to bring a second desired bead dispenser 2 into engagement with the second drive cog 11 disposed on the arm 12 of the carousel 1. Beads from the second bead dispenser 2 can then be dispensed into desired bead receiving chambers of the sample plate 13. This process is can be repeated and/or automated, so that beads from further bead dispensers 2 attached to the carousel 1 are dispensed into further bead receiving chambers in the sample plate 13. In another embodiment, the bead dispensers 2 attached to the carousel 1 can be changed or refreshed during the process of dispensing beads into the sample plate 13.

One or more beads may dispensed from one or more bead dispensers 2 into one or more bead receiving chambers of the sample plate 13 in any desired manner. For example, in one sample well the same species or type of bead (for example, with a specific probe or reagent) may be dispensed into all the bead receiving chambers. In another sample well, pairs of the same species of type of bead may be dispensed into adjacent bead receiving chambers. In one embodiment a single bead is dispensed into each bead receiving chamber and different types of beads (for example, with different probes or reagents) are dispensed into each of the bead receiving chambers of a particular sample well. In another embodiment, one or more of the bead receiving chambers may be left empty. In yet another embodiment, one or more bead receiving chambers may receive more than one bead, such as if the bead has a relatively small diameter relative to other beads which may be dispensed into other bead receiving chambers.

Figure 3:
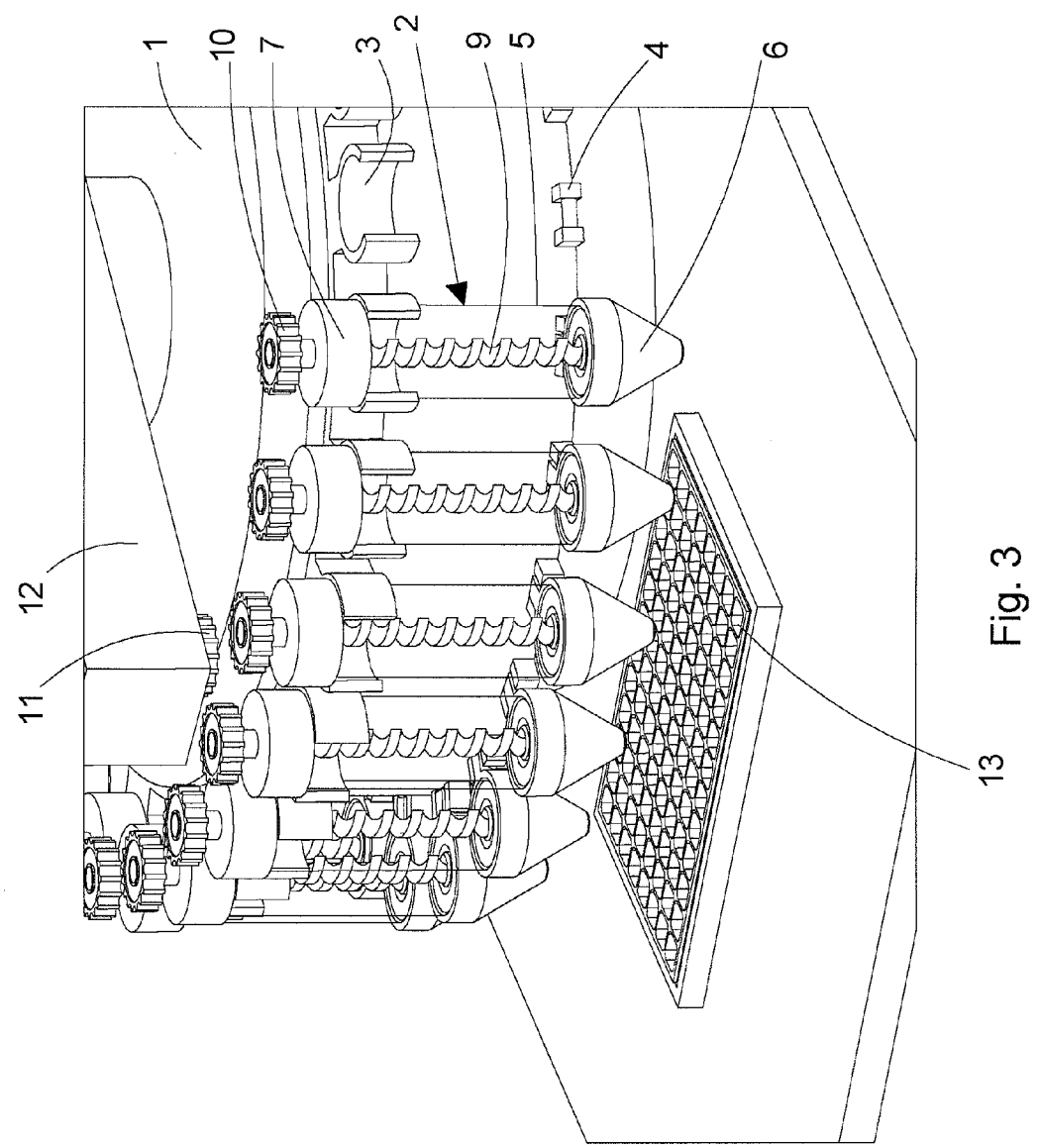
FIG. 3 shows in greater detail a plurality of reagent bead or microsphere dispensers mounted to a carousel and an arm in engagement with a reagent bead or microsphere dispenser according to the first main embodiment of the present invention.

FIG. 3 shows in greater detail a plurality of bead dispensers 2 secured to docking portions on the carousel 1 by a clip 3 and a retaining pin 4. The retaining pin 4 can engage with a hook 8 provided on the dispensing portion 6 of the bead dispenser 2. The retaining pin 4, hook 8 and clip 3 can prevent the body of a bead dispenser 2 from rotating during use. The auger, helical screw or screw thread mechanism 9 within each bead dispenser 2 can be rotated or driven by bringing the teeth of a first cog 10 attached to the spindle or shaft of the auger, helical screw or rotating mechanism 9 into intermeshing or interlocking engagement with a second drive cog or second drive mechanism 11 which preferably depends from the arm 12 of the carousel 1. The second drive cog or second drive mechanism 11 can be driven or rotated by an electric motor.

In another embodiment, a sensor can be disposed on the carousel 1 or otherwise configured in close proximity to the dispensing portion 6 of a bead dispenser 2, a visual detection system may be used to determine whether or not one or more beads have been dispensed or are otherwise correctly located in appropriate bead receiving chambers 15 of a sample plate 13. In one embodiment, the beads may be colored and may contrast with the color of the sample plate 13 which is substantially clear. The sample plate 13 may comprise one or more luminescence or fluorescence markers and a luminescence or fluorescence detecting device may be used to determine whether or not beads have been correctly dispensed into appropriate bead receiving chambers 15 of a sample well 14. A determination may be made, for example, by determining whether or not a bead obscures or obstructs the luminescence or fluorescence markers on the sample plate 13 from being observed or otherwise detected. In another embodiment, a magnetic, electrical, capacitive or mechanical sensor is used to determine the presence or absence of beads in bead receiving chambers 15 of a sample plate 14.

In one embodiment, a control system may be used to determine the number, location, and/or type of beads which have been dispensed into one or more bead receiving chambers 15. The control system may also determine into which bead receiving chambers 15 a bead should be dispensed. Once sample fluid has been dispensed into the central fluid receiving areas of sample wells 14, the control system may check that an appropriate amount of sample fluid has been dispensed and that all the beads are at least partially or are fully immersed by the sample fluid.

The amount of sample fluid to be dispensed into the central fluid receiving area of a sample well 14 may depend upon the number of bead receiving chambers 15 formed within the sample well 14, the diameter of the beads which are dispensed into the bead receiving chambers 15 and the number of beads which are dispensed into any given sample well 14. The control system may be used to vary the amount of sample fluid dispensed into sample wells 14 so that beads are immersed in sample fluid to a substantially constant depth irrespective of the number of beads present in a sample well 14, the number of bead receiving chambers 15 and the diameter of the beads which are dispensed.

Different formats of sample plates 13 may be provided. For example, as shown in FIGS. 1 and 3 the sample plate 13 may comprise a two dimensional array of sample wells 14. For example, the sample plate 13 may comprise a 4×4, 4×6, 4×8, 4×10, 4×12, 6×6, 6×8, 6×10, 6×12, 8×8, 8×10, 8×12, 10×10, 10×12 or 12×12 array of sample wells 14. According to other embodiments the sample plate 13 may comprise a single dimensional strip of sample wells 14. For example, the sample plate 13 may comprise a 4×1, 6×1, 8×1, 10×1 or 12×1 strip of sample wells 14. Yet further embodiments are contemplated wherein the sample wells 14 may be provided in a format other than in an array or strip.

Another embodiment of a bead dispenser is depicted in FIG. 8B, 22, wherein the bead dispenser comprises a plunger guide 26 which is positioned within the body of the syringe body 24. The plunger guide 26 can comprise a screw thread on the outer surface of an upper portion of the plunger guide 26. The inner surface of an upper portion of the syringe body 24 can comprise a complementary screw thread which engages with the screw thread provided on the outer surface of the upper portion of the plunger guide 26 so that the plunger guide 26 is secured or screwed firmly to the syringe body 24. The inner surface of the cap 23 can also comprise a screw thread and the cap 23 can screw onto the upper portion of the plunger guide 26.

A plunger 27 can be located within the plunger guide 26 and the plunger 27 may be depressed by actuating an actuator or plunger boss 28 which is located above the plunger 27 in the bore defined by the plunger guide 26. In one embodiment, an actuator spring (not shown) is provided between the actuator or plunger boss 28 so that when the actuator or plunger boss 28 is depressed, force is transmitted to the plunger 27 via the actuator spring causing the plunger 27 to become depressed. In another embodiment, a return spring (not shown) is provided between the bottom portion of the plunger guide 26 and the plunger 27 so that when the actuator or plunger boss 28 is no longer depressed, both the plunger 27 and the actuator or plunger boss 28 are preferably returned to an upper position.

FIG. 9 shows an exploded view of one embodiment of the bead dispenser 22, such as shown and described above with reference to FIGS. 8A and 8B. FIG. 9 also shows that a silicone member 30 can be provided within the upper portion of the barrel 25. Beads within the syringe body 24 can be funneled or channeled by a helical path formed in the bottom section of the syringe body 24 so that at the bottom of the syringe body 24, beads become arranged in single file or in series. The single file or series of beads can lead into a chamber which is configured immediately above the barrel 25 and below the plunger guide 26. The chamber can be shaped and arranged so as to accommodate a single bead which is positioned in a bore below the plunger 27 and above the barrel 25. In one embodiment, when the plunger 27 is depressed, the plunger 27 pushes a single bead 20A located in the chamber in a downwards direction. The single bead 20A can then be forced by the plunger 27 through the silicone member 30. In one embodiment, the plunger 27 continues to push or urge the bead 20A through the barrel 25 and into a pocket, recess or bore 21 of a sample well 19 which is positioned immediately below the barrel 25 of the bead dispenser 22. The silicone member 30 can prevent the accidental release of beads from the chamber of the bead dispenser 22 into the barrel 25 of the syringe body 24.

In one embodiment, the bottom portion of the syringe body 24 has a helical shape and acts to guide or channel beads towards the chamber disposed in a lower portion of the syringe body 24. The chamber can be arranged so that only a single bead sits above the silicone member 30 at any instance in time. In one embodiment, the chamber is formed in the bore through which the plunger 27 travels and depression of the plunger 27 causes a bead located in the chamber to be urged through the silicone member 30 and into the barrel 25.

A vibration mechanism may optionally be provided and may be configured to act on the outside of the syringe body 24 so as to ensure that beads move down through syringe body 24 to the bottom portion of the syringe body 24 and line up in single file or in series ready to enter the chamber.

Beads may be pre-packed or pre-loaded into the syringe body 24 by, for example, a kit manufacturer or other supplier. Alternatively, an end-user may load the syringe body 24 with beads.

Figure 10:
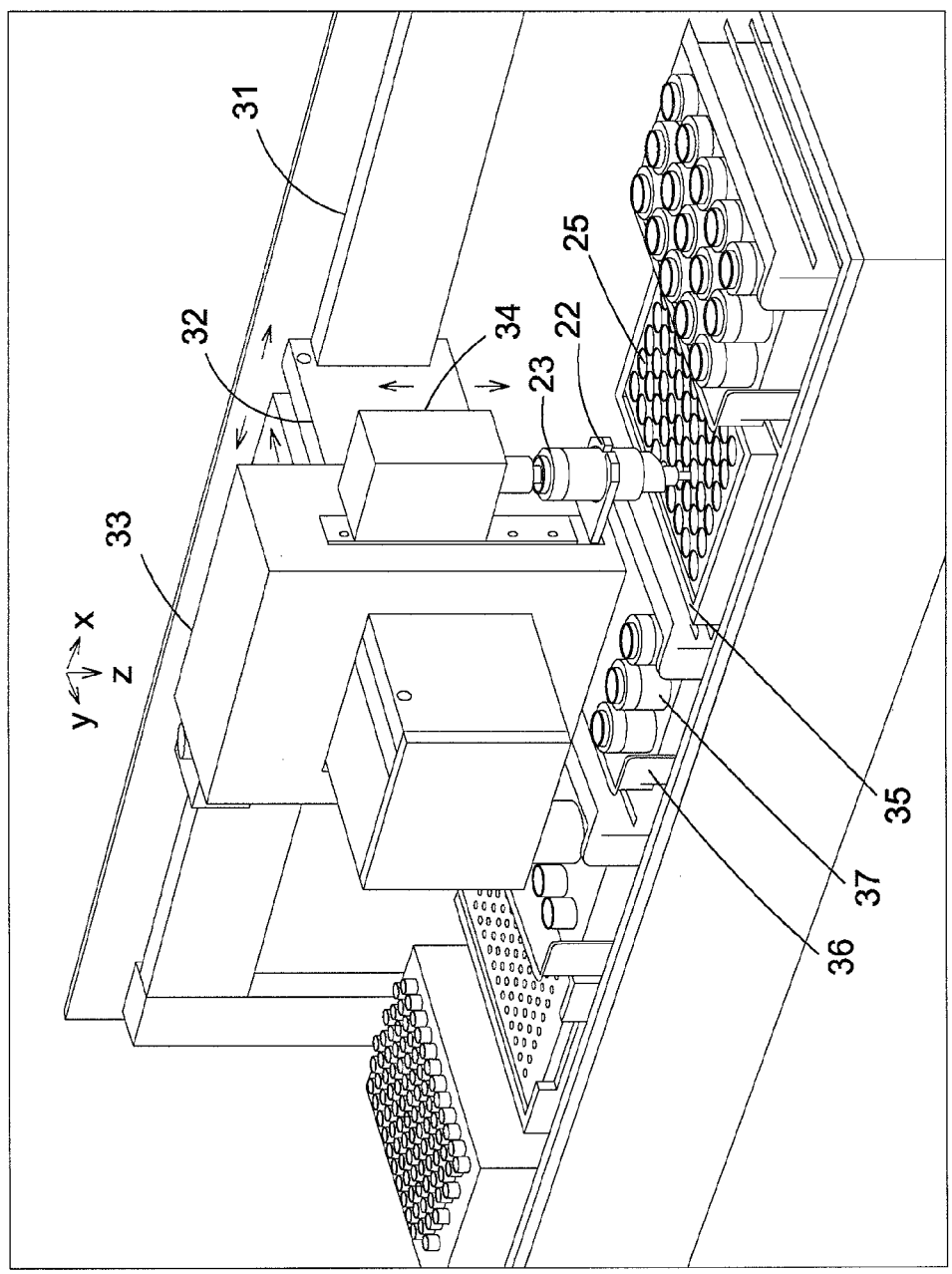
FIG. 10 shows a microarrayer comprising a reagent bead or microsphere syringe pick-up device mounted on an x-y-z translation stage and engaged with a reagent bead or microsphere dispenser above a sample plate.

In another embodiment, a bead dispensing system can comprise a microarrayer or automated apparatus, such as depicted in FIG. 10. As shown in FIG. 10, a plurality of syringe bodies 37 may be loaded onto a tray or pack 36 which is then automatically loaded into the microarrayer or automated apparatus. The tray or pack 36 comprising a plurality of syringe bodies 37 may be moved by a three-axis translation mechanism or robotic arm to a bead dispensing work area of the microarrayer or automated apparatus.

The microarrayer or automated apparatus can comprise a three-axis translation mechanism which comprises a first translation stage comprising a guide rail 31 along which a first arm 32 may be translated in a first (x) horizontal direction. A second translation stage can be provided, and the second translation stage can comprise a mounting block 33 which encompasses or surrounds the first arm 32. The mounting block 33 may be translated in a second (y) horizontal direction (which is preferably orthogonal to the first (x) horizontal direction) and may be moved backwards and forwards along the first aim 32. A third translation stage can be provided and the third translation stage can comprise a body or syringe drive mechanism 34 which houses a linear actuator (not shown). The body or syringe drive mechanism 34 can be slidably mounted on the mounting block 33 and may be raised and lowered in a vertical (z) direction.

In one embodiment, the three-axis translation mechanism further comprises a retractable arm 35 which can extend from the mounting block 33. The three-axis translation mechanism can be programmed to select and pick up a bead dispenser 22, 37 from the tray or pack 36 comprising a plurality of bead dispensers 22, 37. In one embodiment, the body or syringe drive mechanism 34 comprises a tapered spigot which is resiliently mounted within a tubular housing. The spigot can be configured to engage with a tapered portion provided on the syringe cap 23 of the bead dispenser 22, 37. When a bead dispenser 22,37 is positioned in the tray or pack 36 the spigot may be lowered onto the syringe cap 23 of a bead dispenser 22,37 thereby securing the bead dispenser 22, 37 to the body or syringe drive mechanism 34 in a detachable manner. The body or syringe drive mechanism 34 and attached bead dispenser 22, 37 may then be raised to a height such that the retractable aim 35 (which is initially retracted within the body of the mounting block 33) can then be extended. The bead dispenser 22, 37 can then be lowered by the body or syringe drive mechanism 34 so that the upper portion of the syringe body 24 is secured by the retractable arm 35. In one embodiment, the retractable arm 35 can also have an aperture having an internal diameter which is preferably smaller than the outermost diameter of a rim of the upper portion of the syringe body 24.

In another embodiment, each bead dispenser 22, 37 comprises a plurality of identical beads. In yet another embodiment, up to 15 separate bead dispensers 22, 37 may be loaded or provided in a single tray or pack 36 and each of the reagent bead or microsphere dispensers 22, 37 may have a capacity of up to approximately 2000 beads.

In one embodiment, the syringe drive mechanism 34 is configured to pick a bead dispenser 22, 37 out of the tray or pack 36 and will position and lower the barrel 25 of the bead dispenser 22, 37 so that it is immediately above a desired bead pocket or recess 21 provided in a sample well 19 of a sample plate. The syringe drive mechanism 34 can then be actuated so that the actuator or plunger boss 28 of the bead dispenser 22, 37 is depressed which in turn causes the plunger 27 to push a bead 20A from the chamber through the silicone member 30, through the barrel 25 and into the desired bead pocket or recess 21 of the sample well 19. The syringe drive mechanism 34 can be configured to depress the actuator boss 28 and plunger 27 with a desired amount of force as opposed to moving the actuator or plunger boss 28 and plunger 27 to a certain vertical position. As a result, beads 20A can be pressed in tightly and consistently into the bead pockets or recesses 21 of a sample well 19 with a constant amount of force.

Figure 11:
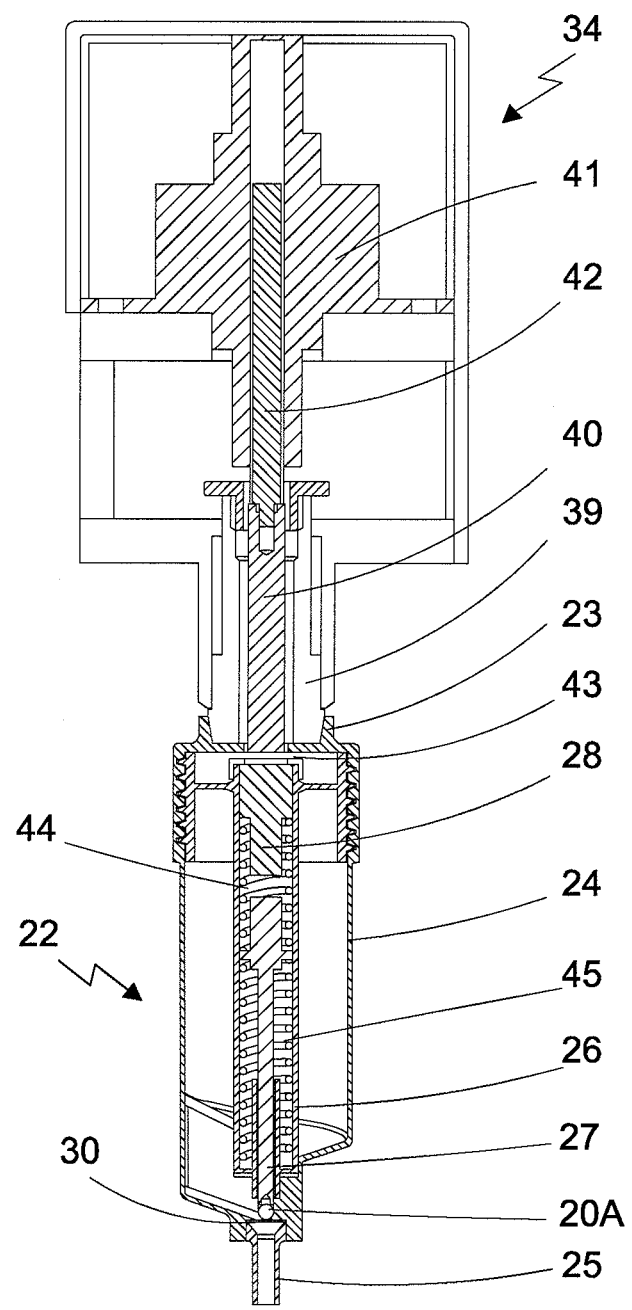
FIG. 11 shows in greater detail a cutaway view of a reagent bead or microsphere syringe pick-up device attached to a reagent bead or microsphere dispenser.

FIG. 11 shows in greater detail an embodiment of a bead dispenser pick-up device or syringe drive mechanism 34 during the process of picking up a bead dispenser 22. The bead dispenser pick-up device or syringe drive mechanism 34 can comprise a spigot 39 having a tapered lower end which is arranged to engage with a tapered recess provided in the upper portion of the syringe cap 23 of the bead dispenser 22. The spigot 39 comprises a central bore through which a plunger push rod 40 is mounted. The plunger push rod 40 is configured to be driven upwards or downwards by a linear actuator 41 which drives a linear actuator lead screw 42 which in turn raises or lowers the plunger push rod 40.

As shown in an embodiment depicted in FIG. 11, to pick up a bead dispenser 22 the bead dispenser pick-up device or syringe drive mechanism 34 is lowered onto the bead dispenser 22 so that the spigot 39 of the bead pick-up device or syringe drive mechanism 34 engages with the syringe cap 23 of the bead dispenser 22. As the bead dispenser pick-up device or syringe drive mechanism 34 is driven downwards onto the bead dispenser 22, the spigot 39 becomes compressed and moves upwards until it is prevented from moving any further upwards. The spigot 39 can be driven further downwards whilst in a compressed state so that the interlocking tapers of the spigot 39 and syringe cap 23 engage causing the bead dispenser 22 to become attached to the bead pick-up device or syringe drive mechanism 34.

In one embodiment, the bead dispenser 22 as shown in FIG. 11 is substantially similar to that shown in FIGS. 8A, 8B and 9 except that the spacer 29 shown in FIGS. 8B and 9 is replaced with a retaining cap 43 in the embodiment shown in FIG. 11. FIG. 11 also shows the location of an actuating spring 44 which is provided between the actuator or plunger boss 28 and the plunger 27 and which transmits force applied to the actuator or plunger boss 28 to the plunger 27. A return spring 45 is also shown and is provided between the plunger 27 and the base of the plunger guide 26 and causes the plunger 27 (and hence also the actuator or plunger boss 28) to return to an upper position when the actuator or plunger boss 28 is no longer depressed or actuated.

Figures 12A, 12B:
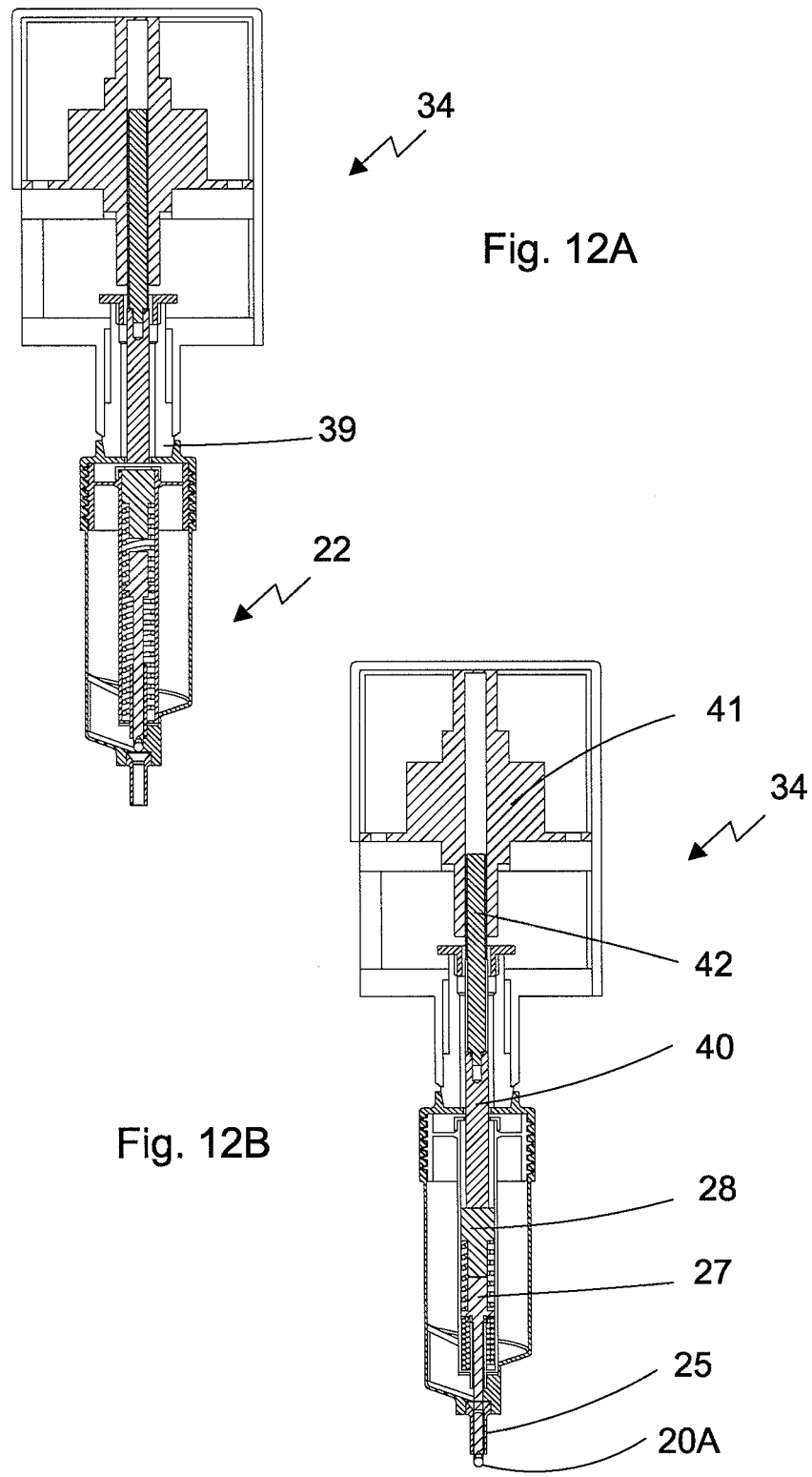
FIG. 12 shows a reagent bead or microsphere A) being transported by a reagent bead or microsphere syringe pick-up device and B) in the process of being dispensed from a reagent bead or microsphere dispenser by a plunger mechanism which is actuated by the reagent bead or microsphere syringe pick-up device.

FIG. 12A shows an embodiment of the bead dispenser pick-up device or syringe drive mechanism 34 which has picked up a bead dispenser 22 and which is in the process of transporting the bead dispenser 22 to a desired location. Once the bead dispenser pick-up device or syringe drive mechanism 34 has engaged with the bead dispenser 22, the bead dispenser pick-up device or syringe drive mechanism 34 is raised so that the spigot 39 is no longer compressed. The spigot 39 returns to a downward position and the bead dispenser 22 including syringe body 24 is locked on to the spigot 39 by the tapers on the spigot 39 and syringe cap 23.

FIG. 12B shows an embodiment of a bead dispenser 22 in the process of dispensing a bead 20A from the bead dispenser 22 into a pocket or recess of a sample well (not shown) of a sample plate (not shown). The linear actuator 41 of the bead dispenser pick-up device or syringe drive mechanism 34 can be actuated and causes the linear actuator lead screw 42 to extend thereby pushing the push rod 40 downwards. The downwards movement of the push rod 40 can depress the actuator or plunger boss 28. The actuator or plunger boss 28 can transmit force to the plunger 27 via the actuating spring 44, by not touching the plunger 27 directly. The plunger 27 can force a bead 20A from a chamber within the central bore provided within the syringe body 24. The bead 20A can be forced through the membrane 30 and down through the barrel 25 and into the recess or pocket of a sample plate (not shown) by the plunger 27.

FIG. 13A shows an embodiment of a bead pick-up device or syringe drive mechanism 34 in the process of ejecting a bead dispenser 22 from the end of the bead pick-up device or syringe drive mechanism 34. In this mode of operation the bead dispenser 22 is positioned above the tray or pack 36. The linear actuator 41 can drive the linear actuator lead screw 42 downwards until the plunger 27 is extended a maximum extent. The spigot 39 can also be extended to the maximum extent. The linear actuator 41 can then continue to apply force via the actuator or plunger boss 28 to the plunger 27, as shown in FIG. 13B, with the result that the body of the bead dispenser 22 is forced off from the end of the tapered spigot 39. The reagent bead or microsphere dispenser 22 can then fall back into the bead dispenser tray or pack 36.

Assays

The sample plate disclosed herein can be used for performing a variety of assays. In one embodiment, the sample plate comprises one or more sample wells, wherein the one or more sample wells comprise one or more bead receiving chambers. In one embodiment, the bead receiving chamber of a sample plate comprises a probe. In yet another embodiment, the bead receiving chamber comprises a bead comprising a probe. In yet another embodiment, the bead receiving chamber is a recess. Thus, in one embodiment, the one or more sample wells comprise a base portion; wherein the base portion comprises one or more recesses. The one or more recesses can comprise a tapered section. In another embodiment, the one or more recesses comprise a recess with a diameter that is less than the diameter of a bead, such as a bead comprising a probe. In one embodiment, the bead present in a recess does not touch the bottom of a well. In another embodiment, the bead present or within a recess does not contact the bottom of a well or a base portion of a sample well. The sample plate can comprises one or more probes or reagents, which can be used to analyze one or more samples.

The sample plate as described herein can be used to assay a sample for one or more analytes. The sample can be a biological sample, such as tissue, blood, serum, urine, saliva, cerebrospinal fluid (CSF), sputum, bone marrow, synovial fluid, aqueous humor, amniotic fluid, cerumen, broncheoalveolar lavage fluid, prostatic fluid, sweat, fecal matter, hair, tears, cyst fluid, pleural and peritoneal fluid, pericardial fluid, lymph, chyme, chyle, bile, interstitial fluid, lavage fluids from sinus cavities, bronchopulmonary aspirates or other lavage fluids. The sample can be processed into a fluid sample which can be added to as sample plate. Samples may be diluted prior to being dispensed into the solid phase or they may be dispensed into deep well microplates, diluted in situ and then the diluted analyte transferred to the functional solid phase. In another embodiment, the sample can be a library of compounds, such as for drug screening. In another embodiment, a sample may comprise a purified protein, a protein complex, or other biological molecule or complex.

In one embodiment, a system comprising one or more bead dispensers and a sample plate as described herein is used for assaying a sample Also provided herein is a method for assaying a sample comprising: providing one or more bead dispensers; providing a sample plate as described herein; and controlling the dispensing of reagent beads or microspheres from the one or more reagent bead or microsphere dispensers into one or more of the sample wells.

In another embodiment, the sample plate as described herein can be used for multiplexing. For example, the sample plate can be used to analyze multiple analytes in a sample. The sample plate can comprise multiple probes, each detecting a different analyte. The sample plate can also be used to detect one or more analytes for one or more samples. In one embodiment, a method of using a sample plate to analyze a sample for multiple analytes comprises providing a sample plate as described here; inserting one or more reagent beads or microspheres into one or more pockets, recesses or bores of a sample well; and adding a sample to the sample well.

In one embodiment, the sample plate is used to perform an assay which detects binding between a probe, such as a probe attached to a bead, and an analyte in a sample. For example, a method of detecting an analyte can comprise adding a sample to a sample plate comprising one or more sample wells, wherein one or more of said sample wells comprise a bead retaining chamber. The bead retaining chamber may be formed from a base portion of a sample well, wherein the base portion comprises one or more recesses. The one or more recesses comprises a bore with a tapered section, or the recess may not comprise a tapered section and may comprise a diameter that is less than the diameter of a bead to be added to, deposited in, or present in the bead retaining chamber. The bead retaining chamber can comprise a probe, and the sample can be incubated with the probe; and binding of an analyte in the sample with the probe can be detected. The sample plate can comprise a plurality of probes, wherein a plurality of analytes is detected. In another embodiment, a plurality of samples is added to the sample plate.

In one embodiment, a bead is coated with a member of a binding pair ("probe"), and the bead is present in a sample plate, such as within a bead retaining chamber. An aliquot of a specimen to be examined can be dispensed into a sample plate and incubated with probe. After washing to remove residual specimen and any interfering materials it may contain, a second binding agent, specific for the analyte and conjugated to an enzyme can be added. During a second incubation any analyte captured onto the solid phase will combine with the conjugate. After a second washing to remove any unbound conjugate, a chromogenic substrate for the enzyme is added. Any enzyme present will begin to convert the substrate to a chromophoric product. After a specified time the amount of product formed may be measured using a spectrophotometer, either directly or after stopping the reaction.

The sample plate can be used to perform an immunoassay, such as based on Enzyme Linked ImmunoSorbent Assay ("ELISA") procedures. A sample plate comprising a member of an antigen-antibody combination can be used to bind the other member of an antigen-antibody combination present in a sample. The binding can the be detected using chromogenic, fluorescent or chemiluminescent materials, or radioactive substances. Thus in one aspect, provided herein is a method of using an Enzyme Linked ImmunoSorbent Assay (ELISA) to detect an antigen or an antibody in a sample comprising: providing a sample plate as described above; inserting one or more reagent beads or microspheres into one or more bead retaining chambers (such as one or more pockets, recesses or bores) of a sample well; and adding a sample to the sample well.

In one embodiment, a method for assaying for one or more analytes of interest in a sample comprises inserting one or more beads into one or more pockets or recesses of one or more sample wells of a sample plate, wherein the one or more pockets or recesses comprise a bore having a tapered section, wherein the bead comprises a probe for assaying the one or more analytes. In another embodiment, the method further comprises one or more of the following steps: (i) incubating the sample plate; (ii) washing the sample plate; (iii) aspirating the sample plate; (iv) adding an enzyme conjugate to the sample plate; (v) adding a visualizing agent to the sample plate; and/or (vi) visually analyzing the sample plate.

The sample plate can also comprise a probe that is a nucleic acid or oligonucleotide, such as a DNA or RNA probe which can detect the presence of complementary DNA or RNA in a sample. A hybridization probe can comprise a fragment of a nucleic acid, such as DNA or RNA, which is used to detect the presence of nucleotide sequences which are complementary to the DNA or RNA sequence on the probe. The hybridization probe can hybridize to single-stranded nucleic acid (e.g. DNA or RNA) whose base sequence allows pairing due to complementarity between the hybridization probe and the sample being analyzed. The hybridization probe may be tagged or labeled with a molecular marker such as a radioactive or fluorescent molecule. The probe can be inactive until hybridization at which point there is a conformational change and the molecule complex becomes active and will then fluoresce (which can be detected under UV light) DNA sequences or RNA transcripts which have a moderate to high sequence similarity to the probe are then detected by visualising the probe under UV light.

Many variants, including fluorogenic and luminogenic substrates for ELISA, direct labeling of the second member of the binding pair with a fluorescent or luminescent molecule (in which case the procedure is not called an ELISA but the process steps are very similar) and nucleic acids or other specific pairing agents instead of antibodies can be used as a probe. The same principles can be used to detect or determine any materials which can form specific binding pairs, for example using lectins, rheumatoid factor, protein A or nucleic acids as one of the binding partners.

The sample plate can thus be used to detect an analyte, such as a biomarker, which can be indicative of a disease or condition. The disease or condition can be a tumor, neoplasm, or cancer, such as breast cancer, ovarian cancer, lung cancer, colon cancer, hyperplastic polyp, adenoma, colorectal cancer, high grade dysplasia, low grade dysplasia, prostatic hyperplasia, prostate cancer, melanoma, pancreatic cancer, brain cancer (such as a glioblastoma), hematological malignancy, hepatocellular carcinoma, cervical cancer, endometrial cancer, head and neck cancer, esophageal cancer, gastrointestinal stromal tumor (GIST), renal cell carcinoma (RCC) or gastric cancer. The disease or condition can also be an inflammatory disease, immune disease, or autoimmune disease, such as inflammatory bowel disease (IBD), Crohn's disease (CD), ulcerative colitis (UC), pelvic inflammation, vasculitis, psoriasis, diabetes, autoimmune hepatitis, Multiple Sclerosis, Myasthenia Gravis, Type I diabetes, Rheumatoid Arthritis, Psoriasis, Systemic Lupus Erythematosis (SLE), Hashimoto's Thyroiditis, Grave's disease, Ankylosing Spondylitis Sjogrens Disease, CREST syndrome, Scleroderma, Rheumatic Disease, organ rejection, Primary Sclerosing Cholangitis, or sepsis. The disease or condition can also be a cardiovascular disease, such as atherosclerosis, congestive heart failure, vulnerable plaque, stroke, ischemia, high blood pressure, stenosis, vessel occlusion or a thrombotic event. The disease or condition can also be a neurological disease, such as Multiple Sclerosis (MS), Parkinson's Disease (PD), Alzheimer's Disease (AD), schizophrenia, bipolar disorder, depression, autism, Prion Disease, Pick's disease, dementia, Huntington disease (HD), Down's syndrome, cerebrovascular disease, Rasmussen's encephalitis, viral meningitis, neurospsychiatric systemic lupus erythematosus (NPSLE), amyotrophic lateral sclerosis, Creutzfeldt-Jacob disease, Gerstmann-Straussler-Scheinker disease, transmissible spongiform encephalopathy, ischemic reperfusion damage (e.g. stroke), brain trauma, microbial infection, or chronic fatigue syndrome. The phenotype may also be a condition such as fibromyalgia, chronic neuropathic pain, or peripheral neuropathic pain. The disease or condition can also be an infectious disease, such as a bacterial, viral or yeast infection. For example, the disease or condition may be Whipple's Disease, Prion Disease, cirrhosis, methicillin-resistant staphylococcus aureus, HIV, hepatitis, syphilis, meningitis, malaria, tuberculosis, or influenza. Viral proteins, such as HIV or HCV-like particles can be assessed in an exosome, to characterize a viral condition.

The sample plate can be used to detect a biomarker that is used to detect the disease or condition. For example, the detection of a biomarker can be used to detect or provide a diagnosis, prognosis of a disease or condition. For example, the sample plate can comprise a probe for a cancer marker, and used to detect the cancer marker in a sample from an individual. The presence, absence, or level of the cancer marker in the sample can be indicative of cancer in the individual. In another embodiment, the sample plate can also be used to monitor a disease or condition. For example, an increased level of the cancer marker, as compared to a control, or compared to an earlier assay for the cancer marker from the same individual, can be indicative of progression of the cancer. In yet another embodiment, the sample plate can be used to in determine a therapy or course of action for a condition. For example, an individual may have a genetic variant which leads to the individual being unable to metabolize certain drugs. The sample plate can be used to detect the genetic variant. In another embodiment, the sample plate may be used to detect a compound, which can be indicative of a drug not being metabolized. The sample plate can also be used to detect the intake of certain drugs or compounds, such as be detecting the drug or by-products of the drug, which can be used for drug testing.

The sample plate can also be used to screen for drugs. For example, the sample plate can comprise a probe that is a target for drug development. The sample plate can then be used to screen a library of compounds. Alternatively, the sample plate can comprise a plurality of probes that comprise a library of compounds that are potential drugs. The sample can comprise a drug target, which is added to the sample plate.

Also provided herein is a kit comprising a sample plate disclosed herein. The kit can comprise one or more components for detecting an analyte or for performing an assay. In one embodiment, a kit for detecting an analyte comprises one or more sample plates and a plurality of beads. The plurality of beads can comprise one or more probes, such as a probe that is a nucleic acid, antibody, antibody fragment, protein, peptide, aptamer, or chemical compound. In another embodiment, a kit for performing an Enzyme Linked ImmunoSorbent Assay (ELISA) procedure is provided. The kit can comprise one or more sample plates as described herein; and a plurality of beads, wherein the beads are coated with a reagent comprising an antibody, an antigen or another biomolecule. In yet another embodiment, the kit can comprise components for performing a nucleic acid probe procedure, wherein the kit comprises one or more sample plates as described herein; and a plurality of beads coated with a nucleic acid, such as a DNA or RNA probe or sequence.

EXAMPLES

Example 1

Assaying Different Reagent Concentrations

A sample plate with nine sample wells was provided (FIG. 7, 19). Each sample well (FIG. 7, 19) comprised ten pockets, recesses or bores (FIG. 7, 21) which were arranged in a circle around a central portion of the sample well. Each of the pockets, recesses or bores were loaded with beads which were coated with different concentrations of reagent. The ten beads in the first sample well were coated with a reagent having a concentration of 10 μg/ml and the ten beads in the second sample well were coated with a reagent having a concentration of 8 μg/ml. The ten beads in the third sample well were coated with a reagent having a concentration of 4 μg/ml and the ten beads in the fourth sample well were coated with a reagent having a concentration of 2 μg/ml. The ten beads in the fifth sample well were coated with a reagent having a concentration of 1 μg/ml and the ten beads in the sixth sample well were coated with a reagent having a concentration of 0.5 μg/ml. The ten beads in the seventh sample well were not coated with a reagent i.e. the concentration was 0 μg/ml. The ten beads in the eighth sample well were coated with different concentrations of reagent and comprised concentrations of 10 μg/ml, 8 μg/ml, 4 μg/ml, 2 μg/ml, 1 μg/ml, 0.5 μg/ml, 0 μg/ml, 0 μg/ml, 0 μg/ml and 0 μg/ml. The ten beads in the ninth sample well had the same concentrations as the reagent beads or microspheres in the eighth sample well and were arranged in the same manner as the reagent beads or microspheres in the eighth sample well.

The reagent beads were coated with a capture antibody comprising sheep IgG and were transported in a bicarbonate buffer containing 0.02% Kathon® preservative.

The sample wells of the sample plate were emptied of the preservative in which the reagent beads or microspheres were transported in and 400 μl of a 1/1000 diluted donkey anti-sheep IgG peroxidise conjugate in a Tris Buffered Saline ("TBS") conjugate diluent buffer was added to each sample well. The sample plate was then incubated at ambient temperature and was subjected to medium intensity vibrations for a period of 45 minutes.

Any unbound conjugate was then aspirated from the sample wells using a single channel wash head of a microarrayer apparatus (DS2®, available from Dynex Technologies). Once any unbound conjugate had been aspirated from the sample wells, 500 μl of 1/20 diluted Tris Buffered Saline wash fluid was then immediately added to each sample well. The wash fluid was then aspirated from the sample wells and the process of washing and aspirating wash fluid from the sample wells was repeated twice more. After the third washing step including aspiration of wash fluid had been completed, 300 μl of luminol (a chemiluminescent marker) was then immediately added to each sample well 19. The sample plate was then incubated in the dark at ambient temperature whilst being subjected to medium intensity vibrations for 15 minutes. The sample plate was then transferred immediately to a reading chamber.

A camera was set to an exposure time of 6 minutes and 30 seconds with a gain of 20. Images were taken at 22 minutes and 29 minutes after luminol had been added. The camera exposure time was then changed to 8 minutes and 37 seconds. Further images were taken at 38 minutes, 47 minutes, 56 minutes and 65 minutes after luminol addition. Analysis of the images showed that the greatest observed signal strength was obtained after 15-22 minutes from luminol addition which is consistent with the luminol decay curve.

Example 2

Antibody Assay

Beads coated with a specific capture antibody are dispensed into pockets, recesses, bores or bead receiving chambers of a sample plate. Sample fluid is added to one or more sample wells of the sample plate. The sample fluid comprises an analyte that is a specific antigen that reacts with the antibody coated on the beads.

The sample is incubated with the beads. After the sample plate is subjected to an incubation step so that antigen-antibody complexes are formed, the sample plate is subjected to one or more washing and aspirate steps to remove any unbound sample fluid and to remove any wash fluid. An enzyme conjugate is then added which binds to the antigen part of any antigen-antibody complexes which have been formed, but which will not bind to antibodies or to the antibody part of an antigen-antibody complex. The sample plate is then incubated before being subjected to one or more washing and aspirating steps. Once the sample plate is subjected to one or more washing and aspirating steps, luminol (or another visualising agent) is added. The sample plate is then aspirated to remove any excess luminol (or other visualising agent). The luminol (or other visualising agent) upon contacting enzymes attached to the antigen part of an antigen-antibody complex breaksdown causing a distinctive color to be produced. The sample plate is analysed and an endpoint determination is made.

While preferred embodiments of the disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A sample plate comprising a sample well, wherein said sample well comprises a base portion, wherein said base portion comprises a plurality of recesses, wherein a bead is located in each recess, each recess having a circular cross-section and comprising:
   (a) a tapered section or
   (b) a diameter less than a diameter of said bead located in said recess.

2. The sample plate of claim 1, wherein said tapered section has a taper of at least about 1°.

3. The sample plate of claim 1, wherein said tapered section has a taper of between 1° and 15°.

4. The sample plate of claim 1, wherein said diameter of said recess is at least about 5% smaller than said diameter of said bead.

5. The sample plate of claim 1, wherein said recess comprises a countersunk portion.

6. The sample plate of claim 1, wherein said sample plate comprises a plurality of sample wells.

7. The sample plate of claim 1, wherein said sample well comprises between 2 and 20 recesses.

8. The sample plate of claim 1, wherein said sample well comprises at least 10 recesses.

9. The sample plate of claim 1, wherein said plurality of recesses is arranged circumferentially around a central portion of said sample well.

10. The sample plate of claim 9, wherein said central portion comprises a central recess.

11. The sample plate of claim 9, wherein said central portion does not comprise a recess.

12. The sample plate of claim 1, wherein said plurality of recesses is arranged in a substantially symmetrical or regular manner.

13. The sample plate of claim 1, wherein said plurality of recesses is arranged in a substantially asymmetrical or irregular manner.

14. The sample plate of claim 1, wherein said plurality of recesses is arranged in a substantially linear manner.

15. The sample plate of claim 1, wherein said plurality of recesses is arranged in a substantially curved manner.

16. The sample plate of claim 6, wherein said plurality of sample wells is arranged in an A×B format, wherein A and B are perpendicular axes, and a number of wells along said A axis is greater than, less than, or equal to a number of wells along said B axis.

17. The sample plate of claim 16, wherein said number of wells along said A axis or B axis is at least 2.

18. The sample plate of claim 17, wherein said number of wells along said A axis or B axis is between 2 and 15.

19. The sample plate of claim 6, wherein at least one of said plurality of sample wells is connected to another sample well of said plurality of samples wells by a frangible region.

20. The sample plate of claim 1, wherein said sample plate comprises a base comprising a docking portion for securing said sample plate to a corresponding docking portion of a plate frame holder.

21. The sample plate of claim 1, wherein each of said beads is attached to a probe.

22. The sample plate of claim 21, wherein said probe is a nucleic acid, antibody, antibody fragment, protein, peptide, aptamer, or chemical compound.

23. The sample plate of claim 21, wherein said probe is an oligonucleotide.

24. The sample plate of claim 21, wherein said sample plate comprises a plurality of probes, wherein a subset of said plurality of probes differs from another subset of said plurality of probes.

25. The sample plate of claim 24, wherein said plurality of probes comprises at least 3 different probes.

26. A bead dispensing system comprising:
   (a) a bead dispenser comprising a plurality of beads;
   (b) a sample plate comprising a sample well, wherein said sample well comprises a base portion, wherein said base portion comprises a plurality of recesses, each recess having a circular cross-section and comprising:
      i) a tapered section or
      ii) a diameter less than a diameter of a bead of said plurality of beads; and (c) a control system configured to control dispensing of said beads from said bead dispenser into respective ones of said recesses.

27. The bead dispensing system of claim 26, wherein said bead dispenser comprises:
   (i) a syringe body comprising an annular chamber surrounding a longitudinal bore, wherein said annular chamber is configured to channel a bead within said annular chamber towards a chamber provided in said bore;
   (ii) a plunger provided within said longitudinal bore; and
   (iii) a barrel or nozzle;
   wherein said plunger is configured to dispense a bead from said chamber into said barrel or nozzle.

28. The bead dispensing system of claim 26, wherein said bead dispenser is configured to dispense said plurality of beads automatically.

29. A method of dispensing beads comprising:
   (a) providing a bead dispenser comprising a plurality of beads;
   (b) providing a sample plate comprising a sample well, wherein said sample well comprises a base portion, wherein said base portion comprises a plurality of recesses, each recess having a circular cross-section and comprising
      i) a tapered section or
      ii) a diameter less than a diameter of a bead of said plurality of beads; and
   (c) controlling the dispensing of said beads from said bead dispenser into respective ones of said recesses.

30. The method of claim 29, wherein said dispensing is performed automatically.

31. A kit for detecting an analyte comprising:
   (a) a plurality of beads; and
   (b) a sample plate comprising a sample well, wherein said sample well comprises a base portion, wherein said base portion comprises a plurality of recesses, each recess having a circular cross-section and comprising
      i) a tapered section or
      ii) a diameter less than a diameter of a bead of said plurality of beads.

32. The kit of claim 31, wherein said plurality of beads comprises one or more probes.

33. The kit of claim 32, wherein said probe is a nucleic acid, antibody, antibody fragment, protein, peptide, aptamer, or chemical compound.

34. The kit of claim 32, wherein said probe is an oligonucleotide.

\* \* \* \* \*